US006172210B1

(12) United States Patent
Wiedmer et al.

(10) Patent No.: US 6,172,210 B1
(45) Date of Patent: *Jan. 9, 2001

(54) DNA ENCODING PHOSPHOLIPID SCRAMBLASE

(75) Inventors: Therese Wiedmer; Peter J. Sims, both of Mequon, WI (US)

(73) Assignee: Blood Center Research Foundation, Milwaukee, WI (US)

( * ) Notice: Under 35 U.S.C. 154(b), the term of this patent shall be extended for 0 days.

This patent is subject to a terminal disclaimer.

(21) Appl. No.: 08/790,186

(22) Filed: Jan. 29, 1997

Related U.S. Application Data

(60) Provisional application No. 06/015,385, filed on Apr. 2, 1996.

(51) Int. Cl.[7] .............................. C12N 9/12; C12N 15/54

(52) U.S. Cl. ........................ 536/23.2; 435/194; 536/23.5

(58) Field of Search .............................. 435/194, 320.1; 536/23.2, 23.5; 530/350, 380

(56) References Cited

U.S. PATENT DOCUMENTS

| | | | |
|---|---|---|---|
| 5,258,497 | 11/1993 | Reutelingsperger et al. | 530/350 |
| 5,552,290 | 9/1996 | Michelson et al. | 435/7.21 |
| 5,561,070 | 10/1996 | Stewart et al. | 436/526 |
| 5,578,565 | 11/1996 | Chao et al. | 514/8 |
| 5,585,380 | 12/1996 | Bianco et al. | 514/263 |

OTHER PUBLICATIONS

Smeets, et al, "Calcium–induced transbilayer scrambling of fluorescent phospholipid analogs in platelets and erythrocytes, ," *Biochem. Biophys. Acta.* vol. 1195, pp. 281–286, 1994.
Devaux, et al, "Maintenance and consequences of membrane phospholipid asymmetry, ," *Chem. Phys. Lipids* vol. 73, pp. 107–120, 1994.
Database, Medline on STN, No. 90158550, Zwall, et al., "Loss of membrane phospholipid asymmetry during activation of blood platelets and sickled cells; mechanisms and physiological significance," *Mol. Cell. Biochem.* vol. 1–2, pp. 23–31, 1989.
Bassé, et al, "Isolation of an Erythrocyte Membrane Protein that Mediates $Ca^{2+}$—dependent Transbilayer Movement of Phospholipid," *The Journal of Biological Chemistry*, vol. 271, No. 29, Issue of Jul. 19, pp. 17205–17210, 1996.
Diaz, et al, "Generation of Phenotypically Aged Phosphatidylserine–Expressing Erythrocyte by Dilauroylphosphatidylcholine–Induced Vesiculation," *Blood*, vol. 87, No. 7 (Apr. 1), 1996; pp. 2956–2961.
Bevers, et al, "Platelet Procoagulant Activity: Physiological Significance and Mechanisms of Exposure," *Blood Reviews*, (1991) 5, 146–154, 1991.

Sims, et al, "Complement Proteins C5b–9 Cause Release of Membrane Vesicles from the Platelet Surface That Are Enriched in the Membrane Receptor for Coagulation Factor Va and Express Prothrombinase Activity," *The Journal of Biological Chemistry*, vol. 263, No. 34, Issue of Dec. 5, pp. 18205–18212, 1988.
Sims, et al, "Assembly of the Platelet Prothrombinase Complex Is Linked to Vesiculation of the Platelet Plasma Membrane," *The Journal of Biological Chemistry*, vol. 264, No. 29, pp. 17049–17057, Apr. 3, 1989.
Chang, et al, "Contribution of Platelet Microparticle Formation and Granule Secretion to the Transmembrane Migration of Phosphatidylserine," *The Journal of Biological Chemistry*, vol. 268, No. 10, Issue of Apr. 5, pp. 7171–7178, 1993.
Kojima, et al, "Production and Characterization of Transformed B–Lymphocytes Expressing the Membrane Defect of Scott Syndrome," *J. Clin. Invest.*, vol. 94, Dec., 1994, 2237–2244.
Bevers, et al, "Defective $Ca^{2+}$–Induced Microvesiculation and Deficient Expression of Procoagulant Activity in Erythrocytes From a Patient With a Bleeding Disorder: A Study of the Red Blood Cells of Scott Syndrome," *Blood*, vol. 79, No. 2, (Jan. 15), 1992, pp. 380–388.
Bevers, et al, "The Complex of Phosphatidylinositol 4, 5–Bisphosphate and Calcium Ions Is Not Responsible for $Ca^{2+}$—Induced Loss of Phospholipid Asymmetry in the Human Erythrocyte: A Study in Scott Syndrome, a Disorder of Calcium–Induced Phospholipid Scrambling," *Blood*, vol. 86, No. 5, (Sep. 1), 1995, pp. 1983–1991.
Hamilton, et al, "Complement Proteins C5b–9 Induce Vesiculation of the Endothelial Plasma Membrane and Expose Catalytic Surface for Assembly of the Prothrombinase Enzyme Complex," *The Journal of Biological Chemistry*, vol. 265, No. 7, Issue of Mar. 5, pp. 3809–3814, 1990.
Verhoven, et al, "Mechanisms of Phosphatidylserine Exposure, A Phagocyte Recognition Signal, or Apoptotic T Lymphocytes," *J. Exp. Med.*, vol. 182, Nov. 1995, 1597–1601.
Martin, et al, "Early Redistribution of Plasma Membrane Phosphatidylserine Is a General Feature of Apoptosis Regardless of the Initiating Stimulus: Inhibition by Overexpression of Bcl–2 and Abl," *J. Exp. Med.*, vol. 182, Nov. 1995, 1545–1556.
Dachary–Prigent, et al, "Physiopathological Significance of Catalytic Phospholipids in the Generation of Thrombin," *Seminars in Thrombosis and Hemostasis*, vol. 22, Nov., 1996, 157–164.
Zwall, et al, "Pathophysiologic Implications of Membrane Phospholipid Asymmetry in Blood Cells," *Blood*, vol. 89, No. 4, Feb., 1997, 1121–1132.

(List continued on next page.)

*Primary Examiner*—Keith D. Hendricks
(74) *Attorney, Agent, or Firm*—Quarles & Brady LLP (57) ABSTRACT

An protein preparation that mediates $Ca^{+2}$ transbilayer movement of phospholipid is disclosed. A recombinantly engineered DNA sequence encoding the protein, an inhibitor of the protein activity, genetically engineered cells with altered protein activity, and therapeutic methods are also disclosed.

5 Claims, 3 Drawing Sheets

OTHER PUBLICATIONS

Wood, et al, "Increased Erythrocyte Phosphatidylserine Exposure in Sickle Cell Disease: Flow–Cytometric Measurement and Clinical Associations," *Blood*, vol. 88, No. 5, Sep.,1996, 1873–1880.

Koopman, et al, "Annexin V for Flow Cytometric Detection of Phosphatidylserine Expression on B Cells Undergoing Apoptosis," *Blood*, vol. 84, No. 5, Sep. 1994, 1415–1420.

Weiss, et al, "Platelet Prothrombinase Activity and Intracellular Calcium Responses in Patients With Storage Pool Deficiency, Glycoprotein IIb–IIIa Deficiency, or Impaired Platelet Coagulant Activity—A Comparison With Scott Syndrome," *Blood*, vol. 89, No. 5, Mar. 1997, 1599–1611.

Sims, et al, "Regulatory Control of Complement on Blood Platelets," *The Journal of Biological Chemistry*, vol. 264, No. 32, Nov., 1989, 19228–19235.

Sims, et al, "Induction of Cellular Procoagulant Activity by the Membrane Attack Complex of Complement," *Seminars in Cell Biology*, vol. 6, 1995, 275–282.

Wiedmer, et al, "On the Mechanism by Which Complement Proteins C5b–9 Increase Platelet Prothrombinase Activity," *The Journal of Biological Chemistry*, vol. 261, No. 31, Nov., 1986, 14587–14592.

McIntyre, et al, "Fluorescence Assay for Phospholipid Membrane Asymmetry," *Biochemistry*, vol. 30, No. 51, Jul. 1991, 11819–11827.

Williamson, et al, "Continuous Analysis of the Mechanism of Activated Transbilayer Lipid Movement in Platelets," *Biochemistry*, vol. 34, No. 33, Mar. 1996, 10448–10455.

Comfurius, et al, "Reconstitution of Phospholipid Scramblase Activity from Human Blood Platelets," *Biochemistry*, vol. 35, No. 24, Mar. 1996, 7631–7634.

Wiedmer, et al, "Complement Proteins C5b–9 Stimulate Procoagulant Activity Through Platelet Prothrombinase," *Blood*, vol. 68, No. 4, Oct. 1986, 875–880.

Wiedmer, et al, "Complement–Induced Vesiculation and Exposure of Membrane Prothrombinase Sites in Platelets of Paroxysmal Nocturnal Hemoglobinuria," *Blood*, vol. 82, No. 4, Aug. 1993, 1192–1196.

Wiedmer, et al, "Participation of Protein Kinases in Complement C5b–9–Induced Shedding of Platelet Plasma Membrane Vesicles," *Blood*, vol. 78, No. 11, Dec. 1991, 2880–2886.

Wiedmer, et al, "Role of Calcium and Calpain in Complement–Induced Vesiculation of the Platelet Plasma Membrane and in the Exposure of the Platelet Factor Va Receptor," *American Chemical Society*, vol. 29, No. 3, 1990, 623–632.

Miletich, et al, "Deficiency of Factor $X_a$—Factor $V_a$ Binding Sites on the Platelets of a Patient With a Bleeding Disorder," *Blood*, vol. 54, No. 5, Nov. 1979, 1015–1022.

Weiss, "Scott Syndrome: A Disorder of Platelet Coagulant Activity," *Seminars in Hematology*, vol. 31, No. 4, Oct. 1994, 312–319.

Toti, et al, "Scott Syndrome, Characterized by Impaired Transmembrane Migration of Procoagulant Phosphatidylserine and Hemorrhagic Complications, Is an Inherited Disorder," *Blood*, vol. 87, No. 4, Feb. 1996, 1409–1415.

Wang, et al, "Activation of the Alternative Complement Pathway by Exposure of Phosphatidylethanolamine and Phosphatidylserine on Erythrocytes from Sickle Cell Disease Patients," *J. Clin. Invest.*, vol. 92, Sep. 1993, 1326–1335.

Kennedy, et al, "Protection of Porcine Aortic Endothelial Cells from Complement–Mediated Cell Lysis and Activation by Recombinant Human CD59," *Transplantation*, vol. 57, No. 10, May 1994, 1494–1501.

Fadok, et al, "Exposure of Phosphatidylserine on the Surface of Apoptotic Lymphocytes Triggers Specific Recognition and Removal by Macrophages," *The Journal of Immunology*, vol. 148, No. 7, Apr. 1992, 2207–2216.

Bruckheimer, et al, "Membrane phospholipid asymmetry: host response to the externalization of phosphatidylserine," *Journal of Leukocyte Biology*, vol. 59, Jun. 1996, 784–788.

Gaffet, et al, "Loss of phospholipid asymmetry in human platelet plasma membrane after 1–12 days of storage," *Eur. J. Biochem.*, vol. 222, Apr. 1994, 1033–1040.

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 188 amino acids
      (B) TYPE: amino acid
      (C) STRANDEDNESS: single
      (D) TOPOLOGY: linear    (ii) MOLECULE TYPE: peptide    (xi) SEQUENCE DESCRIPTION: SEQ ID NO:1:

```
Ala Phe Gln Gly Pro Pro Gly Tyr Ser Gly Tyr Pro Gly Pro Gln Val
 1               5                  10                  15

Ser Tyr Pro Pro Pro Ala Gly His Ser Gly Pro Gly Pro Ala Gly
            20                  25                  30

Phe Pro Val Pro Asn Gln Pro Val Tyr Asn Gln Pro Val Tyr Asn Gln
            35                  40                  45

Pro Val Gly Ala Ala Gly Val Pro Trp Met Pro Ala Pro Gln Pro Pro
        50                  55                  60

Leu Asn Cys Pro Pro Gly Leu Glu Tyr Leu Ser Gln Ile Asp Gln Ile
 65                  70                  75                  80

Leu Ile His Gln Gln Ile Glu Leu Leu Glu Val Leu Thr Gly Phe Glu
                    85                  90                  95

Thr Asn Asn Lys Tyr Glu Ile Lys Asn Ser Phe Gly Gln Arg Val Tyr
                100                 105                 110

Phe Ala Ala Glu Asp Thr Asp Cys Cys Thr Arg Asn Cys Cys Gly Pro
            115                 120                 125

Ser Arg Pro Phe Thr Leu Arg Ile Ile Asp Asn Met Gly Gln Glu Val
        130                 135                 140

Ile Thr Leu Glu Arg Pro Leu Arg Cys Ser Ser Cys Cys Cys Pro Cys
145                 150                 155                 160

Cys Leu Gln Glu Ile Glu Ile Gln Ala Pro Pro Gly Val Pro Ile Gly
                165                 170                 175

Tyr Val Ile Gln Thr Trp His Pro Cys Leu Pro Lys
                180                 185
```

(2) INFORMATION FOR SEQ ID NO:2:

(i) SEQUENCE CHARACTERISTICS:
      (A) LENGTH: 568 base pairs
      (B) TYPE: nucleic acid (C) STRANDEDNESS: double
        (D) TOPOLOGY: linear (ii) MOLECULE TYPE: cDNA (xi) SEQUENCE DESCRIPTION: SEQ ID NO:2:

```
CAGCATTCCA AGGACCTCCA GGATATAGTG GCTACCCTGG GCCCCAGGTC AGCTACCCAC      60
CCCCACCAGC CGGCCATTCA GGTCCTGGCC CAGCTGGCTT TCCTGTCCCA AATCAGCCAG     120
TGTATAATCA GCCAGTATAT AATCAGCCAG TTGGAGCTGC AGGGGTACCA TGGATGCCAG     180
CGCCACAGCC TCCATTAAAC TGTCCACCTG GATTAGAATA TTTAAGTCAG ATAGATCAGA     240
TACTGATTCA TCAGCAAATT GAACTTCTGG AAGTTTTAAC AGGTTTTGAA ACTAATAACA     300
AATATGAAAT TAAGAACAGC TTTGGACAGA GGGTTTACTT TGCAGCGGAA GATACTGATT     360
GCTGTACCCG AAATTGCTGT GGGCCATCTA GACCTTTTAC CTTGAGGATT ATTGATAATA     420
TGGGTCAAGA AGTCATAACT CTGGAGAGAC CACTAAGATG TAGCAGCTGT TGTTGTCCCT     480
GCTGCCTTCA GGAGATAGAA ATCCAAGCTC CTCCTGGTGT ACCAATAGGT TATGTTATTC     540
AGACTTGGCA CCCATGTCTA CCAAAGTT                                        568
```

(2) INFORMATION FOR SEQ ID NO:3:

(i) SEQUENCE CHARACTERISTICS:
        (A) LENGTH: 1266 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

```
CGTGTTGTGT ACGTAAGATT CAGGAAACGA AACCAGGAGC CGCGGGTGTT GGCGCAAAGG      60
TTACTCCCAG ACCCTTTTCC GGCTGACTTC TGAGAAGGTT GCGCAGCAGC TGTGCCCGAC     120
AGTCTAGAGG CGCAGAAGAG GAAGCCATCG CCTGGCCCCG GCTCTCTGGA CCTTGTCTCG     180
CTCGGGAGCG GAAACAGCGG CAGCCAGAGA ACTGTTTTAA TCATGGACAA ACAAAACTCA     240
CAGATGAATG CTTCTCACCC GGAAACAAAC TTGCCAGTTG GGTATCCTCC TCAGTATCCA     300
CCGACAGCAT TCCAAGGACC TCCAGGATAT AGTGGCTACC CTGGGCCCCA GGTCAGCTAC     360
CCACCCCCAC CAGCCGGCCA TTCAGGTCCT GGCCCAGCTG GCTTTCCTGT CCCAAATCAG     420
CCAGTGTATA ATCAGCCAGT ATATAATCAG CCAGTTGGAG CTGCAGGGGT ACCATGGATG     480
CCAGCGCCAC AGCCTCCATT AAACTGTCCA CCTGGATTAG AATATTTAAG TCAGATAGAT     540
CAGATACTGA TTCATCAGCA AATTGAACTT CTGGAAGTTT TAACAGGTTT TGAAACTAAT     600
AACAAATATG AAATTAAGAA CAGCTTTGGA CAGAGGGTTT ACTTTGCAGC GGAAGATACT     660
GATTGCTGTA CCCGAAATTG CTGTGGGCCA TCTAGACCTT TTACCTTGAG GATTATTGAT     720
AATATGGGTC AAGAAGTCAT AACTCTGGAG AGACCACTAA GATGTAGCAG CTGTTGTTGT     780
CCCTGCTGCC TTCAGGAGAT AGAAATCCAA GCTCCTCCTG GTGTACCAAT AGGTTATGTT     840
ATTCAGACTT GGCACCCATG TCTACCAAAG TTTACAATTC AAAATGAGAA AGAGAGGAT     900
GTACTAAAAA TAAGTGGTCC ATGTGTTGTG TGCAGCTGTT GTGGAGATGT TGATTTTGAG     960
ATTAAATCTC TTGATGAACA GTGTGTGGTT GGCAAAATTT CCAAGCACTG GACTGGAATT    1020
TTGAGAGAGG CATTTACAGA CGCTGATAAC TTTGGAATCC AGTTCCCTTT AGACCTTGAT    1080
GTTAAAATGA AAGCTGTAAT GATTGGTGCC TGTTTCCTCA TTGACTTCAT GTTTTTTGAA    1140
AGCACTGGCA GCCAGGAACA AAAATCAGGA GTGTGGTAGT GGATTAGTGA AAGTCTCCTC    1200
```

AGGAAATCTG AAGTCTGTAT ATTGATTGAG ACTATCTAAA CTCATACCTG TATGAATTAA    1260

GCTGTA    1266

(2) INFORMATION FOR SEQ ID NO:4:

(i) SEQUENCE CHARACTERISTICS:
        (A) LENGTH: 422 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:4:

```
Arg Val Val Tyr Val Arg Phe Arg Lys Arg Asn Gln Glu Pro Arg Val
 1               5                  10                  15

Leu Ala Gln Arg Leu Leu Pro Asp Pro Phe Pro Ala Asp Phe Xaa Glu
             20                  25                  30

Gly Cys Ala Ala Ala Val Pro Asp Ser Leu Glu Ala Gln Lys Arg Lys
         35                  40                  45

Pro Ser Pro Gly Pro Gly Ser Leu Asp Leu Val Ser Leu Gly Ser Gly
 50                  55                  60

Asn Ser Gly Ser Gln Arg Thr Val Leu Ile Met Asp Lys Gln Asn Ser
 65                  70                  75                  80

Gln Met Asn Ala Ser His Pro Glu Thr Asn Leu Pro Val Gly Tyr Pro
             85                  90                  95

Pro Gln Tyr Pro Pro Thr Ala Phe Gln Gly Pro Pro Gly Tyr Ser Gly
            100                 105                 110

Tyr Pro Gly Pro Gln Val Ser Tyr Pro Pro Pro Ala Gly His Ser
            115                 120                 125

Gly Pro Gly Pro Ala Gly Phe Pro Val Pro Asn Gln Pro Val Tyr Asn
        130                 135                 140

Gln Pro Val Tyr Asn Gln Pro Val Gly Ala Ala Gly Val Pro Trp Met
145                 150                 155                 160

Pro Ala Pro Gln Pro Pro Leu Asn Cys Pro Pro Gly Leu Glu Tyr Leu
                165                 170                 175

Ser Gln Ile Asp Gln Ile Leu Ile His Gln Gln Ile Glu Leu Leu Glu
            180                 185                 190

Val Leu Thr Gly Phe Glu Thr Asn Asn Lys Tyr Glu Ile Lys Asn Ser
        195                 200                 205

Phe Gly Gln Arg Val Tyr Phe Ala Ala Glu Asp Thr Asp Cys Cys Thr
    210                 215                 220

Arg Asn Cys Cys Gly Pro Ser Arg Pro Phe Thr Leu Arg Ile Ile Asp
225                 230                 235                 240

Asn Met Gly Gln Glu Val Ile Thr Leu Glu Arg Pro Leu Arg Cys Ser
                245                 250                 255

Ser Cys Cys Cys Pro Cys Cys Leu Gln Glu Ile Glu Ile Gln Ala Pro
            260                 265                 270

Pro Gly Val Pro Ile Gly Tyr Val Ile Gln Thr Trp His Pro Cys Leu
        275                 280                 285

Pro Lys Phe Thr Ile Gln Asn Glu Lys Arg Glu Asp Val Leu Lys Ile
    290                 295                 300

Ser Gly Pro Cys Val Val Cys Ser Cys Cys Gly Asp Val Asp Phe Glu
305                 310                 315                 320

Ile Lys Ser Leu Asp Glu Gln Cys Val Val Gly Lys Ile Ser Lys His
```

-continued

```
                    325                 330                 335
Trp Thr Gly Ile Leu Arg Glu Ala Phe Thr Asp Ala Asp Asn Phe Gly
            340                 345                 350

Ile Gln Phe Pro Leu Asp Leu Asp Val Lys Met Lys Ala Val Met Ile
        355                 360                 365

Gly Ala Cys Phe Leu Ile Asp Phe Met Phe Phe Glu Ser Thr Gly Ser
    370                 375                 380

Gln Glu Gln Lys Ser Gly Val Trp Xaa Trp Ile Ser Glu Ser Leu Leu
385                 390                 395                 400

Arg Lys Ser Glu Val Cys Ile Leu Ile Glu Thr Ile Xaa Thr His Thr
                405                 410                 415

Cys Met Asn Xaa Ala Val
            420
```

DNA ENCODING PHOSPHOLIPID SCRAMBLASE

CROSS-REFERENCE TO RELATED APPLICATION

DNA Encoding phospholipid Scramblase, this application is a continuation of provisional application 06/015,385, filed Apr. 2, 1996.

STATEMENT REGARDING FEDERALLY SPONSORED RESEARCH OR DEVELOPMENT

United States Government may have commercial rights under Grant R01 HL36946 from Heart, Lung, & Blood Institue, National Institutes of Health.

BACKGROUND OF THE INVENTION

The exposure of phosphatidylserine (PS) and other aminophospholipids (aminoPL) on the surface of activated or injured blood cells and endothelium is thought to play a key role in the initiation and regulation of blood coagulation. De novo surface exposure of aminophospholipids has also been implicated in the activation of both complement and coagulation systems after tissue injury, and in removal of injured or apoptotic cells by the reticuloendothelial system. Although migration of these phospholipids (PL)from innerto-outer plasma membrane leaflets is known to be triggered by elevated intracellular $[Ca^{2+}]$ $([Ca^{2+}]_i)$ and to be associated with vesicular blebbing of the cell surface, little is known about the cellular constituents that participate in this process.

Role of Cell Surface PS in Coagulation

Several enzyme complexes of the coagulation cascade require assembly on a receptive membrane surface for full expression of catalytic activity (K. G. Mann, et al., *Annu. Rev. Biochem.* 57:915–956, 1988; S. Krishnaswamy, et al.,*J. Biol. Chem.* 267:26110–26120, 1992; P. B. Tracy, *Semin. Thromb. Hemost.* 14:227–233, 1988). In the case of the tenase (FVIIIaFIXa) and prothrombinase (FVaFXa) complexes, this surface catalytic function of the plasma membrane is not normally expressed by quiescent cells, but is rapidly induced upon cell activation (in platelets) or upon cell injury (in platelets, endothelium and other cells) (E. M. Bevers, et al., *Blood Rev.* 5:146–154, 1991; J. Rosing, et al., *Blood* 65:319–332, 1985; E. M. Bevers, et al., *Eur. J. Biochem.* 122:429–436, 1982; E. M. Bevers, et al.,*Biochim. Biophys. Acta* 736:57–66, 1983; T. Wiedmer, et al., *Blood* 68:875–880, 1986). Although specific cell surface protein receptors for FVa and FVIIIa have been postulated, these factors show specific avidity for PS-containing liposomes, and in cell-free systems, this lipid alone can support the catalytic function of the prothrombinase and tenase enzymes (J. Rosing, et al., supra, 1985; M. E. Jones, et al., *Thromb. Res.* 39:711–724, 1985; G. E. Gilbert, et al., *Biochemistry* 3 2:9577–9585, 1993; G. E. Gilbert, et al., *J. Biol. Chem.* 265:815–822, 1990; G. E. Gilbert, et al., *J. Biol. Chem.* 267:15861–15868, 1992). We and others have shown that PS rapidly moves to the surface of plasma membrane upon platelet stimulation, and that this exposure of PS correlates with expression of the platelet's FVa & FVIIIa binding sites and expression of surface catalytic function for tenase and prothrombinase (P. Williamson, et al., *Biochemistry* 31:6355–6360, 1992; F. Basse, et al., *Biochemistry* 32:2337–2344, 1993; C.-P. Chang, et al., *J. Biol. Chem.* 268:7171–7178, 1993; J. Connor, et al., *Biochim. Biophys. Acta* 1025:82–86, 1990; P. Comfurius, et al., *Biochim. Biophys. Acta.* 1026:153–160, 1990). Smeets, et al., *Biochem. Biophys. Acta Biomembr.* 1195:281–286, 1994, Williamson, et al., *Biochem.* 34:10448–10455, 1995; Bratton D. L., *J. Biol. Chem.* 269:22517–22523, 1994). Additional evidence that surface-exposed PS provides the physiological receptor site for these enzyme complexes is provided by (1) the capacity of PS-containing liposomes or phosphoserine to compete binding of FVIIIa to activated platelets (G. E. Gilbert, et al., *J. Biol. Chem.* 266:17261–17268, 1991), (2) the capacity of annexin V and other proteins with affinity for membrane PS to mask the FVa and FVIIIa binding sites expressed by activated platelets (P. Thiagarajan, et al.,*J. Biol. Chem.* 265:17420–17423, 1990; P. Thiagarajan, et al., *J. Biol. Chem.* 266:24302–24307, 1991; J. Dachary-Prigent, et al., *Blood* 81:2554–2565, 1993; J. Sun, et al., *Thromb. Res.* 69:289–296, 1993); (3) evidence that platelets congenitally deficient in inducible FVa and FVIIIa receptors are also defective in stimulated exposure of membrane PS ("Scott syndrome"; see below) (J. P. Miletich, et al., *Blood* 54:1015–1022, 1979; J. Rosing, et al.,*Blood* 65:1557–1561, 1985; P. J. Sims, et al., *J. Biol. Chem.* 264:17049–17057, 1989; S. S. Ahmad, et al.,*J. Clin. Invest.* 84:824–828, 1989; F. Toti, et al.,*Blood* 87:1409–1415, 1996). In addition to the catalytic function PS provides to the prothrombinase and tenase complexes, surface exposed aminophospholipids have been shown to promote the activities of the tissue factor-FVIIa and protein S-activated protein C enzyme complexes of the coagulation system, as well as the activity of the alternative pathway C3-convertase (C3bBb enzyme complex) of the complement system (W. Ruf, et al.,*J. Cell. Biol.* 266:2158–2166, 1991; F. J. Walker, *J. Biol. Chem.* 256:11128–11131, 1981; R. H. Wang, et al.,*J. Clin. Invest.* 92:1326–1335, 1993; P. F. Neuenschwander, et al.,*Biochemistry* 34:13988–13993, 1995).

In addition to the central role that inducible expression of plasma membrane PS is thought to play in the platelet hemostatic response, the surface exposure of PS and phosphatidylethanolamine (PE) in response to membrane injury has been implicated in a variety of thrombotic and inflammatory disorders. For example, repeatedly sickled SS hemoglobin erythrocytes exhibit increased surface exposure of PS, which promotes prothrombinase assembly and accelerates plasma clotting in vitro, and may contribute to thrombotic complications that can arise in sickle cell disease (P. F. Franck, et al., *J. Clin. Invest.* 75:183–190, 1985; N. Blumenfeld, et al., *Blood* 77:849–854, 1991). Increased PE exposure on sickled RBCs (and other cells) has also been shown to promote complement activation with resulting accumulation of C3b/C3d and C5b-9 on the cell surface, potential factors contributing to the accelerated clearance and increased fragility of these cells (R. H. Wang, et al., supra, 1993). PS exposure secondary to immune injury to the endothelium has also been implicated in the thromboembolic complications of hyperacute graft rejection, and PS exposure secondary to C5b-9 accumulation on platelets and red cells has been suggested to contribute to the high risk of venous thrombosis in Paroxysmal Nocturnal Hemoglobinuria (J. L. Platt, et al., *Immunol. Today* 11:450–6; discuss, 1990; A. P. Dalmasso, *Immunopharmacology* 24:149–160, 1992; A. P. Dalmasso, et al., *Am. J. Pathol.* 140:1157–1166, 1992; T. Wiedmer, et al., *Blood* 82:1192–1196, 1993, K. K. Hamilton, et al., *J. Biol. Chem.* 265:3803–3814, 1990; S. P. Kennedy, et al., *Transplantation* 57:1494–1501, 1994)). In the "antiphospholipid syndromes," the interaction of exposed plasma membrane PS and PE with plasma proteins is now generally believed to induce offending antigens (M. D. Smirnov, et al., *J. Clin. Invest.* 95: 309–316, 1995).

Relationship of PS Exposure to Programmed Cell Death

Programmed cell death (apoptosis) is now recognized to be central to the selective elimination of mammalian cells during embryogenesis, tissue re-modeling, and in the clonal selection of immune cells (P. D. Allen, et al., *Blood Rev.* 7:63–73, 1993; J. J. Cohen, *Immunol. Today* 14:126–130, 1993). The apoptotic cell undergoes characteristic changes, including elevated $[Ca^{2+}]_i$, altered phospholipid packing, surface exposure of PS, plasma membrane blebbing and vesiculation, cell shrinkage, chromatin condensation, nucleolar desintegration, and at late stages, DNA degradation by $Ca^{2+}/Mg^{2+}$-dependent endonuclease(s), with characteristic fragmentation into 180 bp multimers ("DNA laddering"). The transcriptional events that initiate apoptosis remain unresolved, but evidence implicates certain proto-oncogenes, including c-myc as activators, and other proto-oncogenes, including bcl-2, as suppressors (P. D. Allen, et al., supra, 1993; J. C. Reed, *J. Cell. Biol.* 124:1–6, 1994). In thymocytes and B-lymphocytes, an apoptotic transformation can be induced by dexamethasone (activating glucocorticoid receptors) and by cAMP (protein kinase A pathway) (D. J. McConkey, et al., *J. Immunol.* 145:1227–1230, 1990; N. Kaiser, et al., *Proc. Natl. Acad. Sci. USA* 74:638–642, 1977; J. J. Cohen, et al., *J. Immunol.* 132:38–42, 1984; R. Merino, et al., *EMBO J.* 13:683–691, 1994; M. K. Newell, et al., *Proc. Natl. Acad. Sci. USA* 90:10459–10463, 1993), as well as directly through treatment with $Ca^{2+}$ionophore (Z.-Q. Ning, et al., *Eur. J. Immunol.* 23:3369–3372, 1993), implicating $[Ca^{2+}]_i$ as a central mediator of the cellular changes that accompany apoptosis. The similarity of the plasma membrane changes noted for apoptotic cells, to those elicited by elevation of $[Ca^{2+}]_i$ in platelets, erythrocytes, and other cells that do not undergo apoptosis, suggest that the nuclear and plasma membrane changes associated with apoptosis are separate "epiphenomena", reflecting independent and unrelated responses to a coordinate rise in $[Ca^{2+}]_i$.

Diaz, et al. (*Blood* 87[7]:2956–2961, 1996) have recently reported the generation of phenotypically aged phosphatidylserine-expressing erythrocytes by dilauroylphosphatidylcholine (DLPC)-induced vesiculation. Red blood cells were artificially vesiculated with DLPC and assessed for alterations in density, membrane lipid asymmetry and propensity to be recognized by macrophages in vitro and the reticuloendothelial system in vivo. The results suggest that vesiculation contributes to alterations is membrane lipid asymmetry and cell characteristics of the aged red blood cell phenotype.

Role of Cell Surface PS in Clearance by the RE System

There is now accumulating data to suggest that cell-surface PS may contribute to the recognition and clearance of senescent, injured, or apoptotic cells by macrophages and other cells of the reticuloendothelial system (J. Savill, et al., *Immunol. Today* 14:131–136, 1993; V. A. Fadok, et al., *J. Immunol.* 148:2207–2216, 1992; J. Connor, et al., *J. Biol. Chem.* 269:2399–2404, 1994). These experiments demonstrate that (i) macrophages have inducible receptors that stereospecifically bind to PS-containing liposomes and to surface-exposed plasma membrane PS; (ii) selective phagocytosis of apoptotic lymphocytes by stimulated macrophages is observed in the absence of plasma proteins, and this can be inhibited by PS-containing liposomes or by phosphoserine (V. A. Fadok, et al., supra, 1992). Consistent with these data, the circulating lifetime of infused PS-containing liposomes is markedly decreased when compared to liposomes devoid of PS, due to rapid hepato-splenic clearance (T. M. Allen, et al., *Proc. Natl. Acad. Sci. USA* 85:8067–8071, 1988). Similarly, increased exposure of plasma membrane PS during in vitro storage of platelet concentrates may contribute to an accelerated clearance of these cells after transfusion (A. P. Bode, et al., *Thromb. Res.* 39:49–61, 1985; A. P. Bode, et al., *J. Lab. Clin. Med.* 113:94–102, 1989; A. P. Bode, et al., *Blood* 77:887–895, 1991; D. Geldwerth, et al., *J. Clin. Invest.* 92:308–314, 1993; P. Gaffet, et al., *Eur. J. Biochem.* 222:1033–1040, 1994; E. M. Bruckheimer, et al., *J. Leukoc. Biol.* 59, 784–788, 1996; C. Diaz, et al, supra, 1996). This possibility is underscored by recent reports documenting increased PS exposure in platelets and red cells during in vitro storage. Evidence that PS exposed on the surface of tumor cells promotes adherence and cytolysis by inflammatory macrophages has also been reported (J. Connor, et al., *Proc. Natl. Acad. Sci. USA* 86:3184–3188, 1989).

Regulation of the Transmembrane Distribution of PS

It is now well established that phospholipids are normally asymmetrically distributed within the plasma membrane of all blood cells, vascular endothelium, and other cells: the aminophospholipids (including phosphatidylserine (PS) and phosphatidylethanolamine (PE)) reside almost exclusively in the inner membrane leaflet, whereas the outer leaflet is enriched in neutral polar phospholipids, including phosphatidylcholine (PC) and sphingomyelin (B. Roelofsen, *Infection* 19:S206–S209, 1992; A. J. Schroit, et al., *Biochim. Biophys. Acta* 1071:313–329, 1991; P. F. Devaux, *Biochemistry* 30:1163–1173, 1991). It is well-recognized that the transmembrane orientation of plasma membrane PL is central to the regulation of surface-localized enzyme reactions of both complement and coagulation systems and to the recognition and phagocytic clearance of injured, aged or apoptotic cells. It is also now generally accepted that the maintenance of PL asymmetry arises through the activity of a specific transmembrane PL "flippase" with specificity for aminoPL. This aminoPL translocase (APT) has been shown to selectively and vectorially transport PS (>PE), but not neutral PL such as PC, from outer to inner leaflets of the plasma membrane in a process that is dependent on both $Mg^{2+}$ and ATP, inhibited by fluoride, o-vanadate or increased $[Ca^{2+}]_c$, and inactivated by N-ethylmaleimide (NEM) or pyridyldithioethylamine (PDA)( M. Bitbol, et al., *Biochim. Biophys. Acta* 904:268–282, 1987; M. Seigneuret, et al., *Proc. Natl. Acad. Sci. USA* 81:3751–3755, 1984; J. Connor, et al., *Biochemistry* 26:5099–5105, 1987; P. F. Devaux, et al., *Phys. Lipids* 73:107–120, 1994; A. Zachowski, et al., *Biochemistry* 25:2585–2590, 1986; C. Diaz, et al., supra, 1996). In addition to plasma membrane, APT activity has also been identified in the membranes of secretory vesicles and synaptosomes (A. Zachowski, et al., *Nature* 340:75–76, 1989). The $K_m$ for ATP is approximately 1 mM, and it has been estimated that one molecule of ATP is hydrolyzed for each aminoPL transported (Z. Beleznay, et al., *Biochemistry* 32:3146–3152, 1993). Two candidate proteins have been proposed to function as APT: the Rh antigen protein, and a 110–120 kDa $Mg^{2+}$-ATPase. Schroit and coworkers (A. J. Schroit, et al., *Biochemistry* 29:10303–10306, 1990) originally proposed that a 32 kDa PS-binding RBC membrane protein that precipitated with antibody to Rh was the erythrocyte APT. Subsequently it was shown that $Rh_{null}$ cells deficient in Rh antigen nevertheless exhibit normal APT activity, and very recently, the 32 kDa PS-binding protein that co-precipitates with Rh protein was identified as stomatin, and it was shown that its interaction with PS was not specific for the aminoPL headgroup. This implies that neither stomatin, nor, the Rh protein can provide APT function (J. Desneves, et al., *Biophys. Res. Commun.* 224:108–114, 1996). The observed similarity in cation, ATP- and PS-dependence of cellular APT activity to a partially purified $Mg^{2+}$-dependent ATPase from RBC led Devaux and associates, and later Daleke, to suggest that APT is a specific $Mg^{2+}$-ATPase (A. Zachowski, et al. supra, 1989; G. Morrot, et al., *FEBS Lett.* 266:29–32; D. L. Daleke, et al., *Ann. NY Acad. Sci.* 671:468–470, 1992; M. L. Zimmerman, et al., *Biochemistry* 32:12257–12263, 1993). Consistent with this premise, Auland (Auland, et al., *Proc. Natl. Acad. Sci* 91:10938–10942, 1994) demonstrated PS-specific transport in proteoliposomes reconstituted with an unidentified $Mg^{2+}$-ATPase isolated from RBC. Recently, an ATPase II from bovine chromaffine granules has been cloned and sequenced, and evidence has been presented that this enzyme may exhibit aminoPL translocase activity (X. J. Tang, et al., *Science* 272:1495–1497, 1996).

$Ca^{2+}$ and the Collapse of Phospholipid Asymmetry

Whereas the rate of spontaneous flip/flop of PL between membrane leaflets is normally quite slow, a substantial rise in $[Ca^{2+}]_c$ resulting from agonist-induced activation, programmed cell death, or, secondary to immune injury, initiates rapid transbilayer migration of all plasma membrane PL with net movement of aminoPL to the outer leaflet, collapsing the normal asymmetric distribution (P. Williamson, et al., *Biochemistry* 31:6355–6360, 1992); F. Basse, et al., *Biochemistry* 32:2337–2344, 1993; C.-P. Chang, et al., supra, 1993; P. Comfurius, et al. *Biochim. Biophys. Acta* 1026:153–160, 1990; A. J. Schroit, supra, 1991; P. Devaux, *Biochemistry* 30:1163–1173, 1991; J. Connor, et al.,*J. Biol. Chem.* 267:19412–19417, 1992). Four different mechanisms have been proposed to account for this induced "scrambling" of plasma membrane PL with net egress of aminoPL to cell surfaces (A. J. Schroit, supra, 1991; P. Devaux, supra, 1992; P. Devaux, supra, 1991; R. F. A. Zwaal, et al., *Biochim. Biophys. Acta* 1180:1–8, 1992): (i) spontaneous collapse of PL asymmetry due to inactivation of vectorial transport by plasma membrane APT; (ii) random scrambling due to transient formation of non-bilayer ($H_{II}$-phase) PL domains upon $Ca^{2+}$-induced blebbing of plasma membrane vesicles; (iii) direct effects of $Ca^{2+}$ on topology and distribution of anionic PLs; (iv) response of a $Ca^{2+}$-sensitive protein(s) that facilitates PL transfer between membrane leaflets.

(i) Spontaneous Collapse of PL Asymmetry

APT is Inhibited at elevated $[Ca^{2+}]_c$, raising the possibility that the concomitant egress of aminoPL to the cell surface simply reflects spontaneous back-leak ("flop") of the PL distribution that is constitutively maintained by APT (P. Williamson, et al., supra, 1992; P. F. Devaux, supra, 1992; P. Devaux, supra, 1991). Nevertheless, inhibition of APT—either by depletion of cellular ATP, or by incubation with fluoride, o-vanadate or NEM—does not in itself cause accelerated transbilayer PL migration or significant cell-surface PS exposure, as long as normally low $[Ca^{2+}]_c$ is maintained (E. M. Bevers, et al., supra, 1991; P. Comfurius, et al. supra, 1990; B. Verhoven, et al., *Biochim. Biophys. Acta* 1104:15–23, 1992; J. Connor, et al. *Biochemistry* 29:37–43, 1990). Conversely, cells genetically deficient in PL scramblase show normal APT activity. Thus it appears that the spontaneous transbilayer migration of plasma membrane PL is inherently very slow at the normal low $[Ca^{2+}]_c$, whereas entry of $Ca^{2+}$ into the cytosol specifically induces rapid movement of PL between plasma membrane leaflets. Whereas the inherent rate of transbilayer migration of PL cannot account for the rapid scrambling observed at elevated $[Ca^{2+}]_c$, it is conceivable that interaction of $[Ca^{2+}]_c$ with APT induces a conformational change that not only inactivates the ATP-dependent inward translocation of aminoPL, but also facilitates selective flop of PS & PE to the outer leaflet. In this context, Bienvenue and associates (Bassé, et al, supra, 1993; Gaffet, et al., *Biochemistry* 34:6762–6769, 1995) have reported evidence for transient vectorial egress of PS upon elevation of $[Ca^{2+}]_c$ in platelet, whereas data from others suggest bidirectional and non-selective transbilayer scrambling of all plasma membrane PL (including PC which is not flipped by APT) at elevated $[Ca^{2+}]_c$ (P. Williamson, et al., supra, 1992; P. Williamson, et al., *Biochemistry* 34:10448–10455, 1995; E. F. Smeets, et al., *Biochim. Biophys. Acta Bio-Membr.* 1195:281–286, 1994; D. Bratton, *J. Biol. Chem.* 269:22517–22523, 1994).

(ii) Relationship of PS Egress to Shedding of Plasma Membrane Vesicles

Data from our laboratory helped establish that surface exposure of PS is intimately related to a process of $Ca^{2+}$-induced vesiculation of the plasma membrane, and that formation of such PS-rich plasma membrane "microparticles" contributes to expression of cellular procoagulant activity (C.-P. Chang, et al., supra, 1993; P. J. Sims, et al., supra, 1989; A. P. Bode, et al., supra, 1985; R. F. A. Zwaal, et al., supra, 1992; T. Wiedmer, et al., supra, 1990; P. J. Sims, et al., *J. Biol. Chem.* 263:18205–18212, 1988; K. K. Hamilton, et al., *J. Biol. Chem.* 265:3809–3814, 1990; H. Sandberg, et al., *Thromb. Res.* 39:63–79, 1985). This correlation between microparticle formation and surface exposure of PS suggested that the membrane fusion events generating these membrane vesicles underlie observed scrambling of plasma membrane PL, presumably through transient formation of $H_{II}$-phase PL (C. P. Chang, et al., supra, 1993). Alternatively, prior egress of PS to the outer leaflet might create a mass imbalance that itself drives plasma membrane evagination and vesiculation (P.F. Devaux, supra, 1991). In this context, we and others have observed that PS migration to the cell surface can precede membrane vesiculation, and can occur without microparticle formation (G. E. Gilbert, et al., *J. Biol. Chem* 266:17261–18269, 1991; F. Basse, et al., *Biochemistry* 32:2337–2344, 1993; P. Gaffet, et al., supra, 1995)). Our data suggested the participation of a calmodulin-dependent kinase in $Ca^{2+}$-induced vesiculation (T. Wiedmer, et al., *Blood* 78:2880–2886, 1991). Involvement of a protein kinase in the cytoskeletal reorganization required for platelet microparticle formation has recently been confirmed (Y. Yano, et al. *Biochem. J.* 298:303–308, 1994). This suggests that whereas membrane fusion may contribute, it neither initiates nor is required for PL scramblase function.

(iii) Interaction of $Ca^{2+}$ With Anionic Plasma Membrane PL

Ion pairing of $Ca^{2+}$ with the anionic PS headgroup might accelerate transbilayer migration by lowering the energy barrier to crossing through the hydrophobic membrane interior. However, $Ca^{2+}$ does not directly induce transbilayer migration of PL in PS-containing membranes, except when mole % of PS is sufficient to induce an $H_{II}$-phase and vesicle-vesicle fusion (A. L. Bailey, et al., *Biochemistry* 33:12573–12580, 1994; B. de Kruijff, et al., *Trends Biochem. Sci.* 5:79–81, 1980). Thus ion pairing of $Ca^{2+}$ with inner leaflet PS would not appear to directly induce PL flip/flop between membrane leaflets. Alternatively, Devaux and associates (J.-C. Sulpice, et al., *J. Biol. Chem.* 269:6347–6354, 1994; J.-C. Sulpice, et al., *Biochemistry* 35:13345–13352, 1996) proposed that $Ca^{2+}$ binding to phosphatidylinositol 4,5-bisphosphate (PIP2) induces transbilayer migration of other PL, based on the observation that adding PIP2 to RBC promoted $Ca^{2+}$-dependent transbilayer movement of PS. Nevertheless, subsequent studies revealed that this incorporation of exogenous PIP2 also induces enough membrane lysis to account for any apparent increase in transbilayer migration of PS (Bevers, et al. *Blood* 86:1983–1991, 1995).

(iv) Role of $Ca^{2+}$-Sensitive Protein(s) in PL Redistribution

Elevation of $[Ca^{2+}]_c$ is known to give rise to marked changes in several cytoskeletal and membrane proteins that might affect the rate of movement of PL between plasma membrane leaflets. For example, several cytoskeletal proteins (including, spectrin and erythrocyte band 4.1) (A. M. Cohen, et al., *Blood* 68:920–926, 1986; S. B. Sato, et al., *Eur. J. Biochem.* 130:19–25, 1983; A. C. Rybicki, et al., *J. Clin. Invest.* 81:255–260, 1988; K. A. Shiffer, et al., *Biochim. Biophys. Acta* 937:269–280, 1988) have been shown to bind specifically to the PS headgroup, and this interaction potentially serves to trap PS in the inner leaflet of the plasma membrane (P. Comfurius, et al., *Biochim. Biophys. Acta* 983:212–216, 1989). Breaking such interactions, as might occur through interaction of $Ca^{2+}$ with the PS headgroup, or through proteolytic degradation of cytoskeletal proteins, would potentially dissociate PS from these endofacial contacts and thereby accelerate PS flop to the outer leaflet (P. F. Franck, et al., supra, 1985). In this context, it has been reported that polyamines inhibit the endogenous PL scramblase activity of the RBC membrane, suggesting that these polycations inhibit interaction of $Ca^{2+}$ at its endofacial membrane site (D. L. Bratton, et al., supra, 1994; J.-C. Sulpice, et al. supra, 1996). Calpain-mediated proteolysis of components of the submembrane cytoskeleton can be temporally-correlated to membrane vesiculation and to surface exposure of PS. Nevertheless, inhibition of calpain does not prevent PS egress, and, $Ca^{2+}$-dependent PL scramblase activity is readily demonstrated in resealed RBC ghosts and inside-out RBC membrane vesicles (IOV) washed free of calpains and other soluble proteases (P. Comfurius, et al., supra, 1990; T. Wiedmer, et al., *Biochemistry* 29:623–632, 1990; Fox, et al., *J. Biol. Chem.* 266:13289–13295, 1991; J. E. B. Fox, et al., *J. Cell Biol.* 111:483–493, 1990; P. F. J. Verhallen, et al., *Biochim. Biophys. Acta* 903:206–217, 1987; L. Dachary-Prigent, et al., *Blood* 81:2554–2565, 1993) On the other hand, the possibility that a membrane protein with inherent PL scramblase activity directly mediates $Ca^+$-induced transbilayer migration of PL was suggested by the observation that this activity is inhibited by sulfhydryl oxidation of membrane proteins with PDA (P. Williamson, et al., supra, 1995). Consistent with this finding, we recently reported the purification and preliminary characterization of an integral RBC membrane protein that, when reconstituted in liposomes, mediates a $Ca^{2+}$-dependent transbilayer movement of PL mimicking plasma membrane PL reorganization evoked upon elevation of $[Ca^{2+}]_c$ (F. Bassé, et al., *J. Biol. Chem.* 271:17205–17210, 1996) Evidence that a protein of similar function must also be present in platelets was recently reported by Zwaal (P. Comfurius, et al., *Biochemistry* 35:7631–7634, 1996).

The Scott Syndrome

Scott syndrome is a bleeding disorder described in a single patient that reflects impaired expression by activated platelets of the membrane sites that are required for normal assembly of the prothrombinase and tenase enzyme complexes (H. J. Weiss, et al., *Am. J. Med.* 67:206–213, 1979; H. J. Weiss, *Semin. Hematol.* 31:1–8, 1994). Platelets obtained from this patient secrete and aggregate normally when exposed to various agonists (ADP, thrombin, collagen, complement proteins C5b-9, or calcium ionophore), but when fully activated, exhibit a marked deficiency of membrane binding sites for factors Va and VIIIa, reflecting a concomitant reduction in the amount of surface-exposed PS (J. P. Miletich, et al., supra, 1979; J. Rosing, et al., supra, 1985; J. P. Sims, et al., supra, 1989; S. S. Ahmad, et al., supra, 1989).

Although Scott syndrome was originally described as an isolated platelet disorder, it is now clear that other blood cells from this patient, including erythrocytes and lymphocytes, are affected as well (E. M. Bevers, et al. *Blood* 79:380–388, 1992). Measurements that have been made by ourselves and others suggest that Scott platelets and erythrocytes contain normal amounts of PS and other phospholipids, and also exhibit normal aminophospholipid translocase activity (H. J. Weiss, et al., 1979). These cells are defective, however, in their capacity to mobilize PS from inner to outer membrane leaflets in response to elevated $[Ca^{2+}]_i$, a response that is now thought to be required for normal prothrombinase and tenase assembly. A search for the molecular defect responsible for the Scott syndrome has to date failed to reveal abnormality in platelet or red cell proteins (probed by 2-dimensional electrophoresis); the agonist-induced elevation of $[Ca^+]$ in Scott platelets is normal; and the calpain and transglutaminase activities of both Scott platelets and RBCs are indistinguishable from normal controls, as assessed by the $Ca^{2+}$-induced cleavage or cross-linking of cytoskeletal proteins (P. Comfurius, et al., *Biochim. Biophys. Acta* 815:143–148, 1985).

We have established in in vitro culture EBV-transformed lymphoblast cell lines from this patient and have demonstrated that these immortalized cells exhibit the same phenotype of impaired $Ca^{2+}$-induced plasma membrane phospholipid scrambling that is characteristic of the platelets and erythrocytes in this disorder. Our data also establish that this defect propagates through multiple cell divisions and can be corrected by heterokaryon fusion with wild-type cells that exhibit normal plasma membrane phospholipid scrambling (H. Kojima, et al. *J. Clin. Invest.* 94:2237–2244, 1994).

Similar data have recently been reported for a second patient with Scott syndrome, and evidence for a familial inheritance of the cellular defect provided (F. Toti, et al., supra, 1996)). This implies that the molecular basis for this clinical disorder relates to a gene defect that results in impaired activity of a cellular protein that is expressed in a variety of cell lineages, and that this protein normally mediates the intracellular $Ca^{2+}$-dependent transbilayer movement (or "scrambling") of plasma membrane phospholipids that occurs in response to cell activation, apoptosis, or cell injury. We identify this protein as "phospholipid scramblase", "PL scramblase", and "P37". We mean for "P37" to be synonymous with "phospholipid scramblase or PL scramblase" and refer to these names interchangeably throughout the text.

The loss of normal PL scramblase function in patients with Scott syndrome may relate to either the abnormal expression of an inhibitor of the activity of PL scramblase, a deletion or loss of function mutation in the gene encoding P37 protein, or, a mutation affecting a cofactor of P37 that is required for normal expression of its PL scramblase activity.

Patients with the Scott syndrome defect display abnormal bleeding and a prolongation of the time required for blood clotting (H. J. Weiss, *Semin. Hematol.* 31:1–8, 1994). This implies that activation of PL scramblase is normally required for effective clot formation and for efficient hemostasis, whereas loss or inhibition of PL scramblase activity leads to retarded blood clotting. We therefore propose that the selective activation of PL scramblase function is of potential therapeutic value in the acceleration of hemostasis and in preventing blood loss, whereas the selective inhibition of PL scramblase function is of potential therapeutic value in certain thrombotic disorders characterized by excessive or inappropriate clot formation due to expression of plasma membrane procoagulant activity.

In this application, we identify the cellular component that functions to mediate the $Ca^{2+}$-dependent reorganization of plasma membrane phospholipids and describe methods for preventing egress of PS to the surface of activated, injured, or apoptotic cells.

BRIEF SUMMARY OF THE INVENTION

The present invention relates to the creation and use of antithrombotic and thrombostatic reagents that depend on the properties of a protein preparation that mediates $Ca^{2+}$ dependent transbilayer movement of membrane phospholipids.

The present invention is a preparation of a protein, wherein the protein is a phospholipid scramblase and wherein the protein is approximately 35–37 KD as measured on a 12.5% SDS-polyacrylamide gel under reducing conditions. Preferably, the scramblase comprises residues 59–90 of SEQ ID NO:1. More preferably, the preparation comprises residues 1–188 of SEQ ID NO:1.

In another embodiment of the present invention, the PL scramblase comprises residues 59–90 of SEQ ID NO:1 with conservative or functionally equivalent substitutions.

In the most preferred embodiment of the present invention, the PL scramblase comprises residues 75–392 of SEQ ID NO:4 with conservative or functionally equivalent substitutions.

The present invention is also a DNA sequence encoding the PL scramblase. Preferably, this DNA sequence comprises the nucleic acids 223–1176 of SEQ ID NO:3.

The present invention is also an inhibitor of the PL scramblase activity of P37. This inhibitor may be an antisense nucleotide derived from the DNA sequence of P37. In another embodiment, the inhibitor is a peptide sequence that is a competitive inhibitor of P37 PL scramblase activity. Preferably, the inhibitor is a peptide that either binds to plasma membrane phosphatidylserine, prevents binding of $Ca^{2+}$ to P37, or prevents its phosphorylation by cellular protein kinases. In another embodiment, the inhibitor is an antibody, preferably a monoclonal antibody, raised against P37.

The present invention is also a method for preventing the surface exposure of plasma membrane phosphatidylserine, phosphatidylethanolamine and cardiolipin on the surface of in vitro stored platelets or red blood cells. This method comprises the steps of adding an inhibitor of P37 PL scramblase activity to the stored platelets or red blood cells.

The present invention is also a method for prolonging survival of transplanted organs comprising the step of adding an inhibitor of P37 PL scramblase activity to an organ perfusate during in vitro organ storage. The present invention is also a method for prolonging the survival of transplanted cells, tissues, and organs by genetically engineering the cells to be transplanted so as to alter their expression of plasma membrane P37 in order to reduce exposure of PS and other thrombogenic phospholipids at the plasma membrane surface, thereby reducing the risk of infarction due to fibrin clot formation.

The present invention is also a method for prolonging the in vivo survival of circulating blood cells (erythrocyte, platelets, lymphocyte, PMN's, and monocytes) comprising the step of preventing surface exposure of plasma membrane phosphatidylserine on the surface of the cells by exposing the blood cells to an inhibitor of P37 PL scramblase activity.

The present invention is also a method for preventing the procoagulant activities of erythrocytes in sickle cell disease comprising the step of inhibiting erythrocyte P37 in a sickle cell patient.

The present invention is also a method for treating autoimmune and inflammatory diseases comprising the step of treating a patient with an inhibitor of the PL scramblase activity of P37.

The present invention is also a method for diagnosing individuals with reduced or elevated capacity for platelet-promoted or erythrocyte-promoted fibrin clot activity comprising the step of quantitating the cellular expression of P37. This quantitation may take the form of immunoblotting using an antibody to P37, an ELISA assay using an antibody to P37, flow cytometric analysis of the binding of monoclonal antibody reactive against the predicted extracellular domain of P37 (residues 386–392 of sequence disclosed in SEQ ID NO:4) or using oligonucleotides derived from P37 cDNA and the polymerase chain reaction. In one method of the present invention, the quantitation is performed by isolating P37 from a patient blood sample, measuring the amount of P37 isolated and comparing the measurement with a control sample. The measurement may be by isolating P37 from a patient blood sample and measuring via densitometry the amount of P37 protein electrophoresed in a stained electrophoretic gel.

It is an object of the present invention to provide a preparation of a PL scramblase.

It is another object of the present invention to provide an inhibitor of P37 PL scramblase activity.

It is another object of the present invention to provide an antithrombotic agent.

It is another object of the present invention to create cells, tissue, and organs for transplantation that have increased potential for survival and reduced potential for causing fibrin clot formation and vascular thrombosis when grafted into a recipient host.

Other objects, advantages and features of the present invention will become apparent after one of skill in the art reviews the specification, claims and drawing herein.

DETAILED DESCRIPTION OF THE INVENTION

The present invention is the purification and characterization of an approximately 35–37 kD membrane protein from human erythrocytes that promotes a $Ca^{2+}$-dependent transbilayer redistribution of membrane phospholipids including PS and PC, with properties similar to the PL scramblase activity that is evoked upon elevation of $Ca^{2+}$ in the cytosol of erythrocytes and other cells. We have named this membrane protein "P37." We mean for "P37" to be synonymous with "phospholipid scramblase or PL scramblase" and refer to these names interchangeably throughout the text. By "phospholipid scramblase or PL scramblase activity," we mean the $Ca^{2+}$ dependent transbilayer movement of plasma membrane phospholipid.

In one embodiment, the present invention is a protein preparation of P37. Preferably, the protein comprises residues 59–90 of SEQ ID NO:1. More preferably, the PL scramblase comprises residues 1–188 of SEQ ID NO:1. Most preferably, the protein comprises residues 75–392 of SEQ ID NO:4.

In another embodiment, the protein comprises conservative substitutions or functionally equivalent residues of the residues described in the paragraph above. By "functionally equivalent" we mean that the equivalent residues do not inhibit or disrupt the activity of the PL scramblase preparation.

The examples below demonstrate one method of isolating P37 from human erythrocytes. After examination of the specification below, other methods of protein isolation will become apparent to one of skill in the art. The examples below also describe an assay for the measurement of PL scramblase activity. A suitable preparation of the present invention would have a PL scramblase activity of at least 10% that of the preparation described below in the examples. Preferably, the activity would be at least 50% that of the examples described below.

The present invention is also a recombinant DNA sequence encoding P37. A preferable DNA sequence encoding P37 would comprise the nucleic acids of SEQ ID NO:2. A more preferable DNA sequence encoding P37 would comprise the nucleic acids 223–1176 of SEQ ID NO:3. One of skill in the art of molecular biology would know how to obtain DNA sequences encoding the PL scramblase. For example, one might sequence P37 directly via standard protein sequencing techniques as we report below in Example C. The peptide sequence could be analyzed to provide oligonucleotide probes for a human cDNA leukocyte library. (One such cDNA library is available from Invitrogen in a pCDNA3 vector.)

Residues 59–90 of SEQ ID NO:1 are the amino acid sequence that we obtained of a cyanogen bromide fragment of the PL scramblase. SEQ ID NO:1 is the translated product of ATCC clone 962235 and is a longer amino acid sequence containing residues 59–90. Residues 75–392 of SEQ ID NO:4 is the predicted full-length sequence of the P37 polypeptide, based on analysis of the open reading frame of SEQ ID NO:3.

By use of probes obtained from other domains of the PL scramblase one would then be able to isolate a cDNA clone encoding the entire P37 protein sequence. Sequence identified as SEQ ID NO:3 contains the entire open reading frame encoding P37 as well as flanking residues of 5' and 3' untranslated sequence. The full-length translation of SEQ ID NO:3 is identified as SEQ ID NO:4. (The symbol Xaa indicates a stop.) Analysis of the open reading frame of this sequence identifies residues 75–392 of SEQ ID NO:4 as comprising the full-length protein sequence of P37. No signal peptide sequence is identified between residues 75–392 of SEQ ID NO:4, indicating that this is also likely to be the length of the mature polypeptide after post-translational processing. The calculated molecular weight of the polypeptide containing residues 75–392 of SEQ ID NO:4 is 35,049 daltons and closely approximates the molecular weight of P37 of 35–37 kDa as estimated by apparent mobility in SDS-PAGE.

Most preferably, the preparation would have at least 90% the activity of the PL scramblase preparation described below.

In one embodiment of the invention, the PL scramblase is isolated from erythrocyte membranes. In another embodiment, the protein is produced by bacteria cells, such as E. coli cells, insect cells, or yeast, preferably in vitro cultures that are transfected with plasmid or viral vectors containing cDNA sequences identified at SEQ ID NO:2 in the correct reading frame (3) or cDNA sequences identified at SEQ ID NO:3 in correct reading frame (1). The vector can be chosen from among protein expression vectors known to those skilled in the art. Preferable viral vectors include retrovirus, adenovirus, and baculovirus vectors.

The present invention is also an inhibitor of the PL scramblase activity of P37. In one embodiment, the inhibitor is an antisense nucleotide derived from the DNA sequence encoding P37. One of skill in the art would know how to create such an antisense nucleotide from the cDNA sequence of P37. In another embodiment, the inhibitor is an antibody, preferably a monoclonal antibody, raised against P37. One of skill in the art would know how to make an antibody preparation from the purified protein preparation described below. For example, one could isolate the purified P37 protein from the electrophoretic gel band and use this preparation to inject into an antibody-producing host, such as a rabbit, sheep, goat, rat, or mouse. In addition to polyclonal immune serum, the antibody-producing splenic lymphocytes from such animals can be obtained to prepare monoclonal antibody reactive with specific peptide segments of P37.

Such methods are well-known to those skilled in the art and include myeloma fusion and the in vitro culture, cloning and selection of the resulting hybridoma cells to obtain monoclonal IgG. In a preferred embodiment, recombinant antibody fragments consisting of antigen-binding Fv or ligated single chain Ig ScFv can be prepared from a cDNA library derived from the polyA mRNA of the immune splenic lymphocytes. In this embodiment, PCR is used to selectively amplify cDNA encoding the CDR3 hypervariable domains of the heavy and light Ig chains, this cDNA is then ligated into appropriate phage expression vectors, and the recombined or fused single chain Fv are then expressed as soluble protein and on the surface of the phage particles that are propagated in E. Coli or other suitable host cell. The resulting express recombined monoclonal Ig Fv on their surface and can be panned and cloned to isolate unique cDNA encoding for specific monoclonal reagents that bind to select epitopes on P37 antigen. This unique cDNA can then amplified and used to express large quantities of the desired monoclonal antibody reagent in an appropriate expression system. In another embodiment, the anti-P37 Fv reagent is humanized to reduce its antigenicity for purposes of injection into a human host. The humanized Fv is prepared by converting the nucleotide segments of the murine-derived cDNA to the homologous human sequence in those segments of the heavy and light chain Ig polypeptides that are flanking on either side of the actual antigen combining site. The methods for preparation of these various recombinant immunoglobulin reagents are well-known to those skilled in the art and are also commercially available in kit form (e.g. Pharamacia ScFv).

In another embodiment, the inhibitor is a peptide derived from P37. This peptide sequence is an antagonist or competitive inhibitor of P37 PL scramblase activity. The inhibitor activity could take the form of competing with the binding of native P37 with plasma membrane phosphatidylserine or competing with native P37 in calcium binding. One of skill in the art would realize that one could examine different peptide fragments of P37 for suitability as a competitive inhibitor.

The present invention is also a method for preventing the surface exposure of plasma membrane phospholipids, such as phosphatidylserine, phosphatidylethanolamine and cardiolipin, on the surface of in vitro stored platelets or red blood cells by adding an inhibitor of the PL scramblase activity of P37 to the stored platelets or red blood cells.

The present invention is also a method for prolonging survival of transplanted organs and grafts comprising the step of adding an inhibitor of P37 PL scramblase activity to an organ perfusate during in vitro organ storage. The present invention is also a method for prolonging the survival of transplanted cells, tissues, and organs by genetically engineering the cells to be transplanted so as to alter their expression of plasma membrane P37 in order to reduce exposure of PS and other thrombogenic phospholipids at the plasma membrane surface, thereby reducing the risk of infarction due to fibrin clot formation.

Therefore, in one embodiment, the present invention is a genetically engineered cell for transplantation into a human or animal wherein the cell has a lowered PL scramblase expression. Preferably, the cell expresses no PL scramblase. Preferably, this cell comprises a nucleotide molecule which is expressed by the cell and which codes for protein inhibiting the activity of PL scramblase. In another preferable embodiment, the promotor of the PL scramblase gene is altered to either increase or decrease the expression of the gene. One of skill in the art of molecular biology would envision methods to create these altered cells.

Preferably, the engineered cell is selected from the group consisting of endothelial cells, fibroblasts, epithelial cells, skeletal cells, cardiac and smooth muscle cells, hepatocytes, pancreatic islet cells, bone marrow cells, astrocytes, and Schwann cells. The present invention is also a prosthesis for implantation in an animal or human having the genetically engineered cells attached thereto. In one embodiment, the prosthesis is a vascular graft.

The present invention is also a method for prolonging the in vivo survival of circulating blood cells comprising the step of preventing surface exposure of plasma membrane phosphatidylserine on the circulating blood cells plasma membrane P37. One may also wish to prevent the procoagulant properties of erythrocytes in sickle cell disease by inhibiting erythrocyte P37 in a sickle cell patient.

The present invention is also a method for treating autoimmune and inflammatory diseases, such as disseminated intravascular coagulation, vascular thrombosis, fibrin generation during cardiopulmonary bypass procedures, rheumatoid arthritis, systemic lupus erythematosus, thrombotic thrombocytopenic purpura, heparin-associated thrombosis, and organ transplant rejection comprising the step of treating a patient with an inhibitor of the PL scramblase activity P37.

The present invention is also a method for diagnosing individuals with reduced or elevated capacity for platelet-promoted or erythrocyte-promoted fibrin clot activity by quantitating the level of cellular expression of P37 in the individual. This method may be performed by using an antibody to P37 in an immunoblot or ELISA method. The method may also be performed using oligonucleotides derived by P37 cDNA in the polymerase chain reaction. In another embodiment, the method may be performed by isolating P37 from a whole blood sample, measuring the amount of P37 isolated and comparing the measurement with a control sample.

One may wish to use the protein preparation of the present invention as a hemostatic agent by topically applying the protein preparation to a wound area in a freely bleeding patient.

EXAMPLES

A. Experimental Procedures

Abbreviations Used

PL, phospholipid(s); PC, phosphatidylcholine; PS, phosphatidylserine; PE, phosphatidylethanolamine; NBD-PC, 1-oleoyl-2-[6(7-nitrobenz-2-oxa-1,3-diazol-4-yl)amino]cap royl-sn-glycero-3-phosphocholine; NBD-PS, 1-oleoyl-2-[6 (7-nitrobenz-2-oxa-1,3-diazol-4-yl)amino]cap royl-sn-glycero-3-phosphoserine; OG, N-Octyl-$\beta$-D-glucopyranoside; $PIP_2$, phosphatidylinositol 4,5-bisphosphate; APLTase, aminophospholipid translocase; IOVs, inside-out vesicles.

Materials

Egg yolk phosphatidylcholine (PC), brain phosphatidylserine (PS), 1-palmitoyl 2-oleoyl phosphatidic acid, 1-oleoyl-2-[6(7-nitrobenz-2-oxa-1,3-diazol-4-yl)amino]cap royl-sn-glycero-3-phosphocholine (NBD-PC) and 1-oleoyl-2-[6(7-nitrobenz-2-oxa-1,3-diazol-4-yl)amino]cap royl-sn-glycero-3-phosphoserine (NBD-PS) were obtained from Avanti Polar Lipids. N-Octyl-$\beta$-D-glucopyranoside (OG) was purchased from Calbiochem. Sodium dithionite ($Na_2S_2O_4$, Sigma) was freshly dissolved in 1 M Tris pH 10 at a concentration of 1 M.

PL Scramblase Isolation

Human erythrocytes were obtained from The *Blood Center of Southeastern Wisconsin*. Washed erythrocytes were lysed in 10 vol of ice cold 5 mM sodium phosphate, 1 mM EDTA, pH 7.4, washed free of hemoglobin, and solubilized at a final protein concentration of 3.5 mg/ml in the presence of 100 mM OG in buffer A (20 mM Tris, 0.1 mM EGTA, pH 7.4). After incubation for 30 minutes at 4° C. with continuous stirring, samples were centrifuged at 100,000×g for 30 minutes. The cytoskeleton-depleted supernatants were loaded on a Poros 20 HQ anion-exchange column (PerSeptive Biosystems) equilibrated with buffer B (20 mM Tris, 0.1 mM EGTA, 50 mM OG, pH 7.4). Elution was performed with a gradient of 0–400 mM NaCl in buffer B. Active fractions were pooled, subjected to a buffer exchange by PD 10 gel filtration (Pharmacia) into buffer C (50 mM acetate, 0.1 mM EGTA, 50 mM OG, pH 5.0), and loaded on a Poros 20 HS cation-exchange column (PerSeptive Biosystems) equilibrated in buffer C. The breakthrough fraction was passed through a PD 10 column equilibrated in buffer D (25 mM PIPES, 1 mM $CaCl_2$, 50 mM OG, pH 6.0) and loaded on a Reactive Red 120 6% agarose column (Sigma). Elution was performed with a gradient of 0–1.5 M NaCl in buffer D. Active fractions were pooled and further purified on a Bio-Sil SEC-250 size exclusion column (Bio-Rad) equilibrated with buffer D in which $CaCl_2$ was replaced by 0.1 mM EGTA. Due to losses encountered through size exclusion chromatography, enriched fractions of PL scramblase were routinely prepared by replacing this step by a second anion exchange fractionation on Mono Q (Pharmacia). All column chromatography procedures were performed at room temperature on a BioCAD 20 perfusion chromatography workstation (PerSeptive Biosystems).

Reconstitution into Proteoliposomes

A mixture of PC and PS (9:1 molar ratio) was dried under a stream of nitrogen and resuspended in buffer E (100 mM Tris, 100 mM KCl, 0.1 mM EGTA, pH 7.4) by vigorous vortexing. Protein samples were mixed with liposomes at a final lipid concentration of 4 mg/ml in the presence of 60 mM OG. Detergent was removed by dialysis overnight at 4° C. against 200 vol of buffer E containing 1 g/L SM2-Biobeads (BioRad).

Labeling of Proteoliposomes With NBD-PL

Proteoliposomes were labeled with fluorescent NBD-PC or NBD-PS (0.25 mole %) selectively incorporated into outer, inner, or both membrane leaflets (E. M. Bevers, et al., supra, 1995; J. C. McIntyre and R. G. Sleight, *Biochemistry* 30:11819–11827, 1991). Outer leaflet-labeled proteoliposomes were prepared by addition of NBD-PL (in DMSO) to the pre-formed proteoliposome suspension. Symmetrically-labeled proteoliposomes were prepared by adding NBD-PL to the PC-PS mixture in $CHCl_3$, before drying lipids under nitrogen (above). Addition of protein sample in OG and dialysis against buffer E was then performed as above. Proteoliposomes with fluorescent NBD-PL located exclusively in the inner leaflet of the bilayer were obtained by incubating symmetrically-labeled proteoliposomes with 20 mM dithionite for 1 minute, in order to chemically and irreversibly quench fluorescent analogs located in the outer leaflet (J. C. McIntyre and R. G. Sleight, *Biochemistry* 30:11819–11827, 1991). Vesicles were gel filtered in buffer E to remove unincorporated material and used immediately for assay of PL scramblase activity.

PL Scramblase Activity

PL scramblase activity was measured using a modification of an assay previously described (E. M. Bevers, et al., supra, 1995; J. C. McIntyre and R. G. Sleight, supra, 1991). Routinely, NBD-PL outside-labeled proteoliposomes (0.4 mg/ml PL final concentration) were incubated at 37° C. in buffer E in presence or absence of 2 mM $CaCl_2$. At times indicated in figure legends, proteoliposomes were diluted 25-fold in buffer E containing 4 mM EGTA, and transferred to a stirred fluorescence cuvet at 23° C. Initial fluorescence was recorded (SLM Aminco 8000 spectrofluorimeter; excitation at 470 nm, emission at 532 nm), and 20 mM dithionite added with fluorescence continuously monitored for total of 90 seconds. The difference in residual (non-quenchable) fluorescence observed for samples preincubated at 37° C. in presence vs. absence of 2 mM $CaCl_2$ was attributed to $Ca^{2+}$-induced change in NBD-PL located in the outer leaflet, and hence accessible to dithionite (J. C. McIntyre and R. G. Sleight, supra, 1991). Maximum (100%) dithionite quenching was determined by addition of 1% Triton X-100. In all cases, NBD fluorescence was corrected for photobleaching (<6%; measured in absence of dithionite). Ionized $[Ca^{2+}]$ (FIG. 4) was calculated using FreeCal version 4.0 software (generously provided by Dr. Lawrence F. Brass, University of Pennsylvania, Philadelphia, Pa.).

Trypsination

Samples containing active PL scramblase were incubated for 3 hours at 37° C. in the presence of 2 μg/ml trypsin in 100 mM Tris, 0.1 mM EGTA, pH 8.4, and the reaction was stopped by addition of 1 mM diisopropylfluorophosphate. Samples incubated in absence of trypsin or in presence of trypsin plus 4 μg/ml soybean trypsin inhibitor served as controls. Residual PL scramblase activity of each sample was then determined following reconstitution into NBD-PS outside-labeled liposomes. Residual PL scramblase detected in trypsin-treated samples was normalized to that observed for identically matched samples incubated without trypsin.

Preparation of Erythrocyte IOVs

Erythrocyte inside out vesicles (IOVs) were prepared essentially by methods described by Steck and Kant (T. L. Steck and J. A. Kant, *Methods Enzymol.* 31a:172–180, 1974) with minor modifications. Assays for acetylcholinesterase (outside) and glyceraldehyde 3-phosphate dehydrogenase accessibility (inside) (T. L. Steck and J. A. Kant, supra, 1974) confirmed that >90% of these IOVs were properly oriented and resealed.

PL Scramblase Activity in IOVs

IOVs were suspended in 10 mM Tris, 140 mM KCl, 7.5 mM NaCl, 0.1 mM EGTA, pH 7.4 at 100 μg protein/ml. NBD-PLs (PC or PS) were added to a final 0.25 mole % of total PL. After incorporation of label, IOVs were incubated in presence 0–2 mM $CaCl_2$ for 15 minutes at 37° C. For each sample, percentage of NBD-PL displaced from the external to inward-facing membrane leaflet was determined by the BSA "back-exchange" method as previously described (E. M. Bevers, et al., supra, 1995). PL scramblase activity was evaluated by comparing the amount of NBD-PL moved to the inward-facing leaflet of IOVs in the presence of $Ca^{2+}$ to that observed in the presence of 0.1 mM EGTA. Transport of dithionite by erythrocyte membrane anion exchanger precludes use of this quencher to monitor NBD-PL distribution in IOVs (T. Pomorski, et al., *Mol. Membr. Biol.* 11:39–44, 1994).

B. Results and Discussion

Purification and Membrane Reconstitution of Erythrocyte PL Scramblase

Human erythrocyte membrane proteins depleted of cytoskeleton were solubilized with OG and initially fractionated by anion exchange chromatography. Each eluting fraction was reconstituted into PL vesicles and then 0.25 mole % NBD-PS added to the outer leaflet. After incubation in the presence of either 0 or 2 mM $Ca^{2+}$, the time-dependent distribution of NBD-PS between inner and outer leaflets was determined (see Experimental Procedures and below). A $Ca^{2+}$-dependent movement of NBD-PS from outer to inner membrane leaflets was detected in only those vesicles reconstituted with proteins eluting from Poros 20 HQ between 125 mM-200 mM NaCl. Such activity was not detected in any other column fraction, including those enriched with the predominant erythrocyte membrane band 3 protein, nor was this activity found in unbound flow-through fractions (not shown). Of note, erythrocyte band 3 protein has been reported to exhibit intrinsic "flipping activity" for anionic PL, based on the capacity of the anion transport inhibitor 4,4'-diisothiocyanostilbene-2,2'-disulfonic acid to further attenuate the slow spontaneous ($Ca^{2+}$-independent) migration PL across the erythrocyte membrane (A. Vondenhof, et al., *Biochemistry* 33:4517–4520, 1994).

Figure 1A:
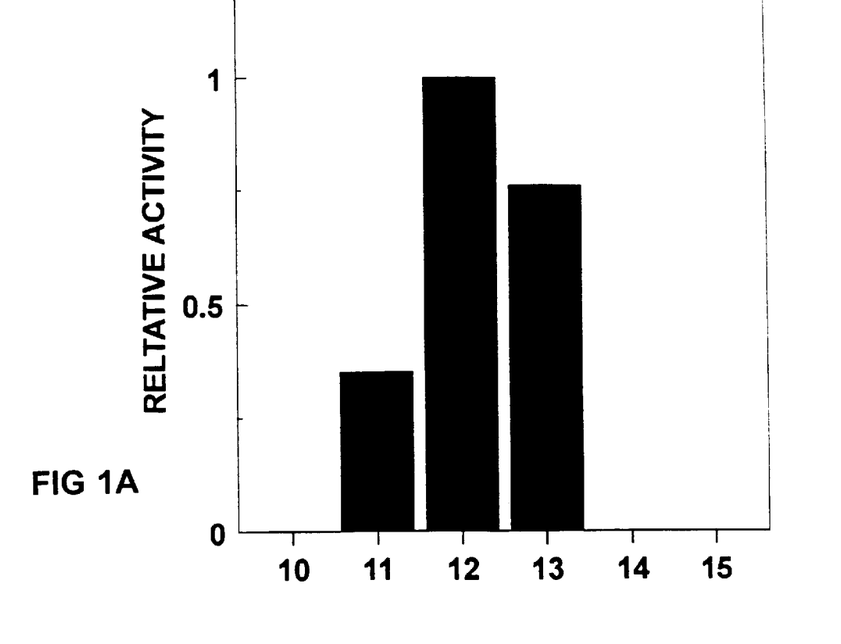
FIG. 1A is a bar graph depicting the amount of PL scramblase activity as a function of chromatography column fraction number.
Figure 1B:
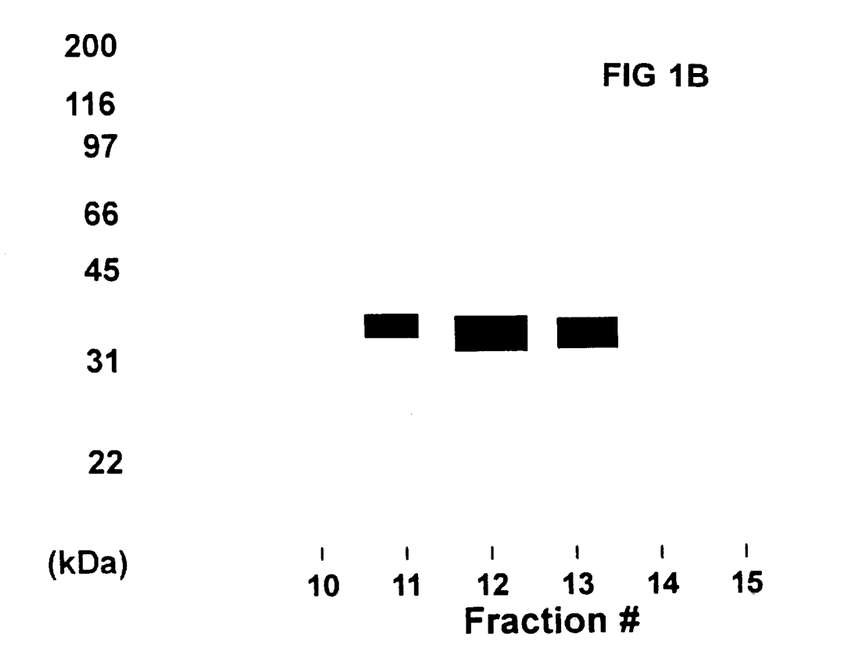
FIG. 1B represents a 12.5% SDS-PAGE in which the fractions described in FIG. 1A have been electrophoresed. The actual 37 kD bands are depicted by dark rectangles.

Through subsequent purification, this PL scramblase activity was found to co-purify with a ~37 kDa protein band that we were able to enrich to apparent homogeneity (FIG. 1). FIG. 1 illustrates final stage of purification of erythrocyte PL scramblase activity. Pool of activity eluting from Reactive Red 120 was concentrated and applied to a 600×7.5 mm BioSil SEC250 column. Flow rate was 0.2 ml/min and 1.0 ml fractions were collected. 100 μl aliquots of each column fraction were reconstituted into liposomes containing NBD-PS exclusively in the outer leaflet and assayed for PL scramblase activity. Samples were also concentrated 10-fold and analyzed by 12.5% SDS-PAGE under reducing conditions, developed with silver staining. Relative PL scramblase activity is plotted directly above the corresponding gel lane. Only data for fractions eluting about peak of activity (fraction #12) are shown. See Experimental Procedures. Fractions 11 and 13 contained additional bands not represented in FIG. 1B.

The activity of this PL scramblase was destroyed by trypsin (Table 1), confirming that activity detected in the reconstituted proteoliposome derived from the purified protein fraction, and not other potentially co-eluting material. In this context, PL scramblase activity has recently been attributed to an interaction of $Ca^{2+}$ directly with membrane lipid. As noted above (Introduction), Sulpice, et al. (J. C. Sulpice, et al., supra, 1994) concluded that $Ca^{2+}$-binding to $PIP_2$ located in the inner leaflet of the erythrocyte membrane induces transbilayer PL scrambling, although this conclusion was not supported by a subsequent study (E. M. Bevers, et al., supra, 1995). Alternatively, Bratton proposed that cytoplasmic polyamines contribute to maintenance of PL asymmetry by shielding anionic head groups from $Ca^{2+}$, and that enhanced transbilayer movement of PL might arise through loss of polyamine-membrane associations at increased intracellular $Ca^{2+}$ (D. L. Bratton, supra, 1994). Although our studies do not address a potential influence of these cytoplasmic components on PL scramblase activity, it should be noted that polyamines would be removed through our lysis and solubilization procedures. Finally, sensitivity of PL scramblase to inactivation by trypsin (Table 1) excludes the possibility that the activity we observe arises from contaminating $PIP_2$ or polyamine. Although data of FIG. 1 and Table 1 suggest that PL scramblase is a low abundance integral membrane polypeptide of ~37 kDa, we cannot now exclude the possibility that observed activity resides in a trace co-purifying membrane protein that goes undetected by silver staining.

Characteristics of PL Transport Mediated by Isolated PL Scramblase

Figure 2:
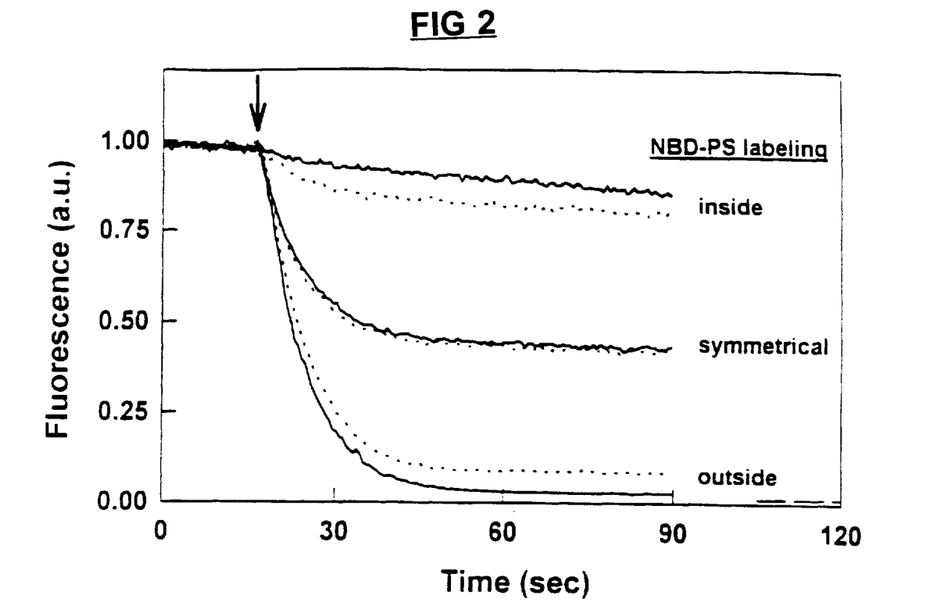
FIG. 2 is a diagram of the bidirectional movement of NBD-PS across lipid bilayers reconstituted with P37.

Proteoliposomes reconstituted with purified PL scramblase remained impermeant to dithionite and stable to spontaneous NBD-PS exchange in absence of $Ca^{2+}$ (FIG. 2).

FIG. 2 illustrates bidirectional movement of NBD-PS across lipid bilayers reconstituted with PL scramblase. PL scramblase was reconstituted into 90% PC, 10% PS membranes trace-labeled with 0.25% NBD-PS, initially located either in the inner membrane leaflet (inside-labeled), randomly distributed between leaflets (symmetrically-labeled), or exclusively in the outer leaflet (outside-labeled). Vesicles were incubated 3 hours at 37° C. in presence of either 0.1 mM EGTA (dotted lines) or 2 mM $Ca^{2+}$ (solid lines) and reaction stopped with EGTA. Distribution of NBD-PS in outer leaflet was determined by quenching with 20 mM dithionite, time of addition indicated by arrow (see Experimental Procedures). Ordinate denotes NBD fluorescence, normalized to t=0; abscissa denotes fluorescence acquisition time (sec). Dashed line indicates level of fluorescence detected after addition of 1% Triton X-100 to each vesicle suspension in presence of dithionite (100% quenching). In this experiment, observed $Ca^{2+}$-dependent transbilayer movement of NBD-PS equaled 8±2% (inside labeled), 0±1% (symmetrically-labeled), and 8±1% (outside-labeled). FIG. 2 illustrates the data of single experiment, representative of at least three separate experiments so performed.

As also illustrated by FIG. 2, $Ca^{2+}$-induced PL scramblase activity was observed to be bidirectional, induced sequestration of NBD-PS initially distributed only in the outer membrane leaflet equaling induced exposure of NBD-PS initially distributed only in the inner leaflet. In proteoliposomes prepared with NDD-PS randomly distributed between membrane leaflets, no movement of probe was detected upon $Ca^{2+}$ addition, consistent with one-for-one PL exchange between membrane leaflets. Similar results were obtained when NED-PC substituted for NBD-PS, and movement of either NBD-labeled PL was unaffected by replacement of matrix PS by phosphatidic acid (data not shown). These results imply that the PL scramblase activity exhibited by lipid vesicles reconstituted with this 37 kDa protein is non-selective for PS versus PC, and facilitates both inward and outward movement of PL between membrane leaflets. Assuming that movement of PL initiated by addition of $Ca^{2+}$ arises through activation of only those proteins oriented to expose $Ca^{2+}$-binding site(s) at the external face of the liposome, these data imply that each PL scramblase mediates bidirectional and non-selective one-for-one exchange of PL between membrane leaflets. Although it has been suggested that elevation of cytosolic $Ca^{2+}$ initiates a vectorial movement of PS and PE from inner to outer plasma membrane leaflets (Bassé, et al., supra, 1993; P. Gaffet, et al., supra, 1995), more recent data suggest that this apparent egress of inner leaflet PS arises through random bidirectional exchange of PL residing in both leaflets of the plasma membrane (P. Williamson, et al., supra, 1992; E. F. Smeets, et al., supra, 1994; P. Williamson, et al., supra, 1995), consistent with the activity we observe in PL scramblase reconstituted proteoliposomes. The fact that these proteoliposomes remain impermeant to dithionite (see FIG. 2), excludes the possibility that this apparently random and bidirectional movement of lipid arises through lytic disruption of lipid bilayer. Nevertheless, we cannot exclude the possibility that an initially vectorial transport of PL in these small vesicles is masked by a counterbalancing exchange to maintain mass balance between membrane leaflets, as might be imposed by head group packing constraints.

The mechanism by which $Ca^{2+}$ interaction with this protein initiates transbilayer movement of PL remains unresolved. To be noted, we observed only a requirement for $Ca^{2+}$ with no requirement for either $Mg^{2+}$ or ATP. In presence of 2 mM $Ca^{2+}$, lipid movement catalyzed by PL scramblase obeyed pseudo-first order kinetics with initial rates that increased with concentration of protein, consistent with a facilitated transport or carrier mechanism (FIG. 3).

Figure 3:
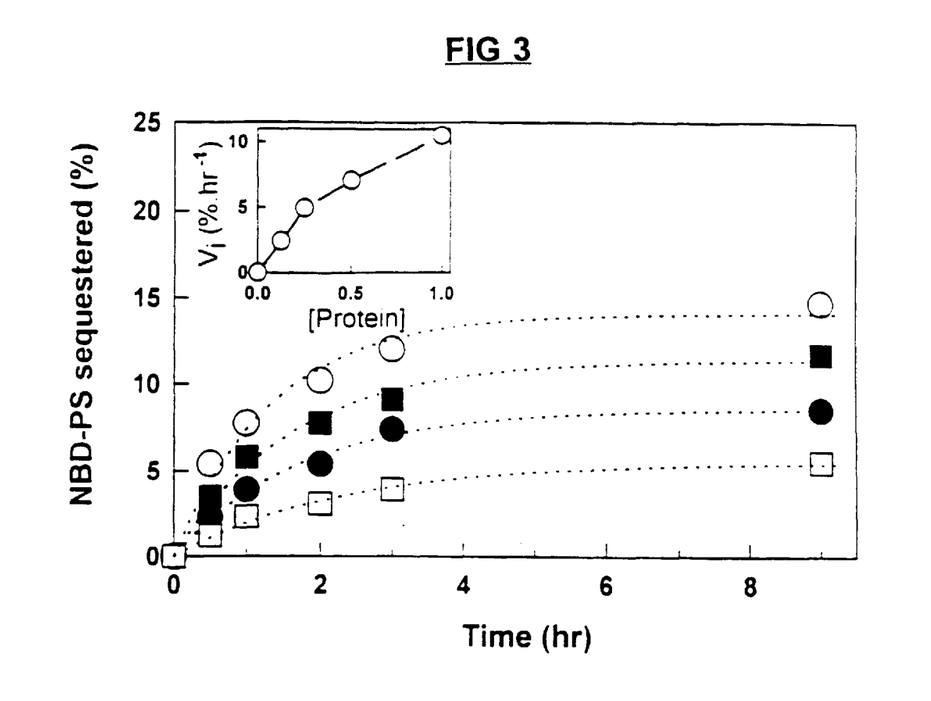
FIG. 3 is a graph describing the kinetics of PS translocation by reconstituted P37.

FIG. 3 diagrams the kinetics of PS translocation by reconstituted PL scramblase. Proteoliposomes were prepared with a constant amount of PL and 2-fold dilutions of purified PL scramblase (Experimental Procedures). NBD-PS (0.25 mole %) was added to outer leaflet and labeled proteoliposomes incubated at 37° C. in presence of 2 mM $Ca^{2+}$. At times indicated (abscissa) samples were analyzed for the amount of NBD-PS that migrated from outer to inner leaflets, according to assay shown in FIG. 2. All data are corrected for spontaneous transbilayer migration of NBD-PS ($\leq 1\%$ $hr^{-1}$) measured for identical samples incubated with 0.1 mM EGTA, substituting for $Ca^{2+}$. FIG. 3 illustrates the data at highest protein concentration (○); 2-fold (■); 4-fold (●) and 8-fold dilutions (□) are indicated. Experimental points at each protein concentration were fitted to first-order exponential rate equation (Sigma Plot; dotted lines). Insert: Derived initial rates ($V_i$; ordinate) plotted against normalized protein concentration (abscissa). Data of single experiment, representative of two so performed.

Derived rate constants for transbilayer lipid movement (at 37° C.) ranged between 0.45–0.74 $hr^{-1}$ over an eight-fold range of protein/lipid ratio. Whereas this activity deviated from anticipated linearity with increased added protein per lipid (insert, FIG. 3), this may reflect an inherent limitation in efficiency of protein reconstitution into the liposome membrane (below). The apparent rate of $Ca^{2+}$-evoked transbilayer movement attained in the reconstituted system ($t_{1/2}$~2 hr; FIG. 3) is approximately one-fourth of the observed rate of PL scrambling ($t_{1/2}$~10.5 hr; P. Williamson, et al., supra, 1992) induced in $Ca^{2+}$-ionophore treated erythrocytes, suggesting somewhat reduced activity in the reconstituted system. Whether this reduced activity reflects partial denaturation of PL scramblase, or, our inability to incorporate amounts of this protein equivalent to that present in the erythrocyte membrane, remains to be determined.

Calcium Dependence

Figure 4:
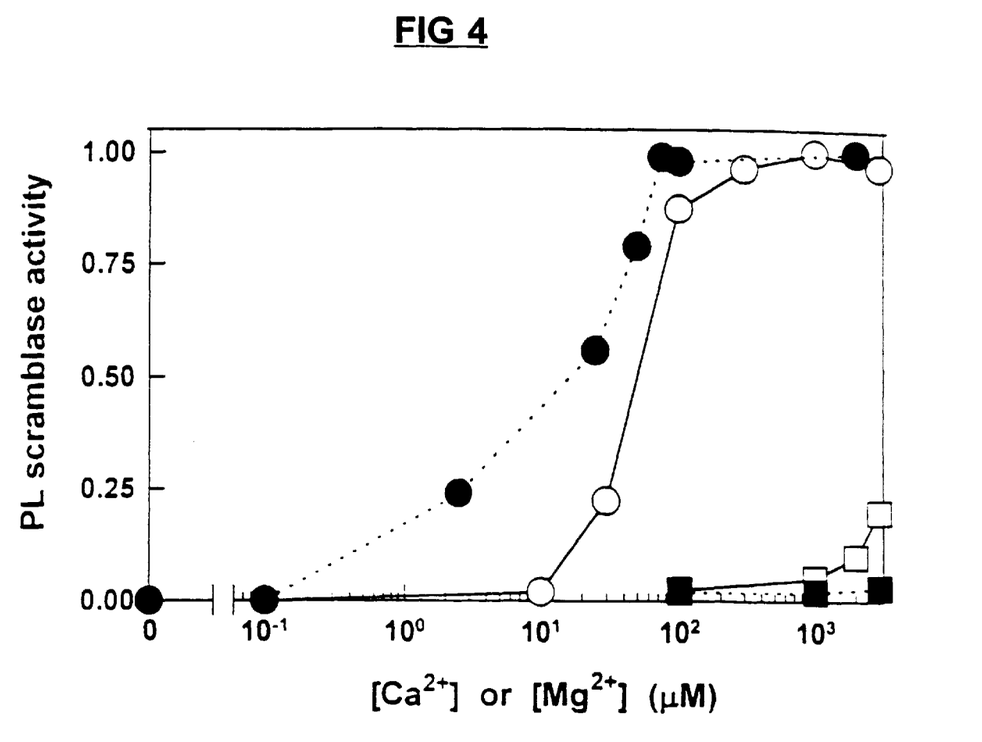
FIG. 4 is a graph describing calcium dependence of P37 activity in proteoliposomes and in erythrocyte IOVs.

In order to confirm that the activity of reconstituted PL scramblase mimicked intrinsic PL scramblase activity of the erythrocyte membrane, we compared [$Ca^{2+}$]-dependence of PL movement in proteoliposomes reconstituted with purified protein to that observed in erythrocyte IOVs (FIG. 4). FIG. 4 diagrams $Ca^{2+}$ dependence of PL scramblase activity in proteoliposomes & erythrocyte IOVs. PL scramblase activity of reconstituted proteoliposomes (closed symbols) and erythrocyte IOVs (open symbols) was determined as described in Experimental Procedures, and plotted as function of external free [$Ca^{2+}$] (●○). Data for each sample were normalized to maximum PL scramblase activity, measured at 2 mM $Ca^{2+}$. Squares (■○) denote PL scramblase activity detected when $Mg^{2+}$, substituted for $Ca^{2+}$. Data of single experiment, representative of three so performed.

In both IOVs and isolated protein reconstituted liposomes, PL scramblase activity was found to obey a sigmoidal dose-response to $Ca^{2+}$, with saturation at ~100 $\mu$M [$Ca^{2+}$], and half-maximal activities attained between 20–60 $\mu$M $Ca^{2+}$. In both cases, little effect of $Mg^{2+}$ was observed. These results are similar to data previously reported for $Ca^{2+}$-induced movement of plasma membrane PL in ionophore-treated erythrocytes, resealed erythrocyte ghosts, and other cells (H. Kojima, et al., *Biochemistry* 33:4517–4520, 1994; B. Verhoven, et al., *Biochim. Biophys. Acta* 1104:15–23, 1992).

PL scramblase activity found in erythrocyte membranes is also observed in platelets, lymphocytes and other cells and is thought to play a central role in initiation of fibrin clot formation and in recognition of apoptotic and injured cells by the reticuloendothelial system. It is not known whether the same protein is responsible for PL scramblase activity found in other cells, or whether such proteins are cell-specific. A protein common to all blood cells is suggested by the observation that the genetic defect in PL scramblase activity arising in Scott syndrome affects all hematologic lineages. Further insight into the cellular distribution of the 37 kDa protein that we have now isolated from normal erythrocytes awaits purification of sufficient protein for sequencing, and to develop specific antibodies.

TABLE 1

Inactivation of PL scramblase by trypsin

| Treatment | | PL scramblase |
| --- | --- | --- |
| Trypsin | Soybean Trypsin Inhibitor | activity[a] (% of control) |
| – | – | (100) |
| – | + | 100 |
| + | – | 13 |
| + | + | 100 |

[a]PL scramblase in response to 2 mM $Ca^{2+}$, expressed as percent of activity of untreated control. Incubation with trypsin and reconstitution of digested protein into liposomes for PL scrambase assay are detailed under Experimental Procedures. Range of measured activities ± 5%. Representative of two separate experiments.

[a]PL scramblase in response to 2 mM $Ca^{2+}$, expressed as percent of activity of untreated control. Incubation with trypsin and reconstitution of digested protein into liposomes for PL scrambase assay are detailed under Experimental Procedures. Range of measured activities ± 5%. Representative of two separate experiments.

C. Amino Acid and Nucleotide Sequence of the PL Scramblase

We purified the PL scramblase by the methods described above. The resulting protein was subjected to further purification by sodium dodecyl sulfate polyacrylamide gel electrophoresis, the protein band visualized by staining with Coomassie brilliant blue, and a slice of the wet gel containing the P37 protein band migrating between ~35–37 kDa excised. This gel slice was sent to the Protein and Carbohydrate Structure Facility at University of Michigan, Ann Arbor, Mich. for cyanogen bromide digestion and internal peptide sequencing. Peptide sequence was obtained from a 2 kD cyanogen bromide fragment derived from the protein contained in the gel slice. The amino acid sequence we obtained is disclosed in residues 59–90 of SEQ ID NO:1.

We obtained an exact match for these residues with a translation product of a cDNA reported in Genbank at AA14325. This sequence includes the predicted methionine (residue 58 of SEQ ID NO:1) located 5' to the preferred locus of cyanogen bromide peptide bond cleavage, yielding a total of 33 residues of continuous identity between the deduced partial internal sequence from P37 and the translation product of the cDNA clone reported in Genbank at AA143025. The entire nucleotide sequence of this cDNA clone (ATCC 962235) is reported at SEQ ID NO:2. Sequence reported at SEQ ID NO:1 is the entire translated sequence of SEQ ID NO:2, using the correct translation reading frame that we deduced from comparison of the CDNA clone with residues 58–90 of SEQ ID NO:1.

Using methods standard to those skilled in the art, we probed human leukocyte, B-lymphocyte, fetal adrenal, and K562 (a human erythro-leukemic cell line) cDNA libraries by PCR, using oligonucleotide primers designed to anneal specifically to SEQ ID NO:2. The PCR reactions revealed that cDNA overlapping SEQ ID NO:2 of the expected number of residues was contained in each of these cDNA libraries. This result indicates that mRNA encoding sequence contained in P37 protein purified from human erythrocyte membrane is also expressed in multiple human cell lines of both erythroid and non-erythroid origin. Based on evidence for the relative abundance of cDNA overlapping SEQ ID NO:2 in the Clontech lambda gt11 K562 library, we selected this library to amplify additional cDNA sequence flanking SEQ ID NO:2.

Using methods standard to those skilled in the art, we PCR amplified the flanking DNA sequences 5' and 3' to sequence ID NO:2 from the K562 lambda gt11 cDNA library (Clontech, Inc) with oligonucleotide primers designed to anneal to sequence ID NO:2 in combination with oligonucleotide primers designed to anneal to regions of the Clontech lambda gt11 vector in the vicinity of the multiple cloning site of the vector. The resulting PCR-amplified cDNA was purified and sequenced. From these PCR-amplified 5' and 3' flanking sequences, partial overlapping identities were found in cDNA reported in Genbank at AA143025, AA056199, AA054476, AA151006, AA171663, D61890, H42131, R76171, R66275, R82537, W90481 and these multiple sequences used in combination with direct sequence obtained from our PCR products to deduce and to confirm the sequence reported at SEQ ID NO:3.

SEQ ID NO:4 is the entire translated sequence of SEQ ID NO:3, using the correct translation reading frame that we deduced from comparison of the cDNA clone with peptide residues 58–90 of SEQ ID NO:1.

The open reading frame of the sequence reported at SEQ ID NO:3 predicts a polypeptide of 318 amino acids (identified as residues Met75-Trp392 of SEQ ID NO:4) with the calculated molecular weight of 35,049 and theoretical isoelectric point (pI)=4.83. This closely approximates the experimentally-estimated molecular weight and isoelectric point of P37 PL scramblase purified from erythrocyte membranes. We therefore identify residues 75–392 of SEQ ID NO:4 as P37, the human plasma membrane PL scramblase and deduce that this same protein is expressed in both erythroid and non-erythroid human cells.

Analysis of the sequence contained in P37 (identified as residues 75–392 of SEQ ID NO:4) predicts a membrane protein with a cytoplasmic N-terminus and a single transmembrane helix formed by residues 365–383, with residues 384–392 projecting from the cell surface and residues 75–364 internal to the cell. A site for phosphorylation by protein kinase C or other serine/threonine protein kinase is predicted at P37 Thr residue 235 (all residue numbers for P37 given according to sequence identified at SEQ ID NO:4). It has been observed that the activity of PL scramblase is reduced in cells depleted of ATP (Martin, et al., *J. Biol. Chem.* 270:10468–10474, 1995), and that inhibitors of $Ca^{2+}$/calmodulin kinases reduce platelet plasma membrane microparticle formation (Wiedmer, et al., Blood 78:2880–2886, 1991), which is consistent with the regulation of the activity of PL scramblase by a phosphorylation of P37 mediated by one or more intracellular protein kinases.

What is claimed is:

1. A recombinant DNA sequence encoding a phospholipid scramblase comprising residues 1–188 of SEQ ID NO: 1.

2. A recombinant DNA sequence encoding a phospholipid scramblase comprising residues 75–392 of SEQ ID NO: 4.

3. A recombinant DNA sequence encoding a phospholipid scramblase wherein said DNA sequence comprises nucleotides 223–1176 of SEQ ID NO: 3.

4. The sequence of claim 1, comprising SEQ ID NO: 3.

5. A recombinant DNA sequence encoding a phospholipid scramblase, wherein said DNA sequence comprises SEQ ID NO: 2 and wherein the sequence is part of a protein expression vector.

* * * * *

UNITED STATES PATENT AND TRADEMARK OFFICE
CERTIFICATE OF CORRECTION

PATENT NO. : 6,172,210 B1
DATED : January 9, 2001
INVENTOR(S) : Therese Wiedmer et al.

It is certified that error appears in the above-identified patent and that said Letters Patent is hereby corrected as shown below:

Title page,
The correct inventorship is Therese Wiedmer, Peter J. Sims, and James G. Stout.

Signed and Sealed this

Twentieth Day of October, 2001

Attest:

*Nicholas P. Godici*

NICHOLAS P. GODICI
*Acting Director of the United States Patent and Trademark Office*

*Attesting Officer*